(12) United States Patent
Freudenthal et al.

(10) Patent No.: US 11,339,425 B2
(45) Date of Patent: May 24, 2022

(54) SYSTEMS AND METHODS FOR BIOLOGICAL ANALYSIS

(71) Applicant: LIFE TECHNOLOGIES CORPORATION, Carlsbad, CA (US)

(72) Inventors: Jacob K. Freudenthal, San Jose, CA (US); Geoffrey Dahlhoff, Menlo Parl, CA (US); Kevin Maher, Woodside, CA (US); Ming Song Chen, Singapore (SG); Gary Lim, San Francisco, CA (US); Ronald Danehy, Shirley, MA (US); David Fortescue, San Francisco, CA (US); Ming Shen, Singapore (SG); Woon Liang Soh, Singapore (SG); Francis T. Cheng, Palo Alto, CA (US); Ruoyun Wu, Singapore (SG); Thiam Chye Lee, Singapore (SG); Gary A. Chappell, San Francisco, CA (US); Chee Kiong Lim, Singapore (SG); Jeff Dere, Saratoga, CA (US); Ted Straub, Burlingame, CA (US); Jorge Fonseca, East Palo Alto, CA (US); Kuan Moon Boo, Singapore (SG); Soo Yong Lau, Singapore (SG)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 143 days.

(21) Appl. No.: 16/382,294

(22) Filed: Apr. 12, 2019

(65) Prior Publication Data
US 2019/0300936 A1    Oct. 3, 2019

Related U.S. Application Data

(62) Division of application No. 14/348,504, filed as application No. PCT/US2012/058096 on Sep. 28, 2012, now Pat. No. 10,323,274.

(Continued)

(51) Int. Cl.
| | |
|---|---|
| *C12Q 1/686* | (2018.01) |
| *B01L 3/00* | (2006.01) |
| *B01L 7/00* | (2006.01) |

(52) U.S. Cl.
CPC .......... *C12Q 1/686* (2013.01); *B01L 3/50855* (2013.01); *B01L 3/50857* (2013.01);
(Continued)

(58) Field of Classification Search
None
See application file for complete search history.

(56) References Cited

U.S. PATENT DOCUMENTS

| 4,652,127 A | 3/1987 | Ekholm et al. |
| 6,600,943 B1 | 7/2003 | Kiuchi |

(Continued)

FOREIGN PATENT DOCUMENTS

| CN | 1595114 A | 3/2005 |
| CN | 101945706 A | 1/2011 |

(Continued)

OTHER PUBLICATIONS

European Communication issued in European Patent Application No. 12 784 373.8, dated Apr. 1, 2019.
(Continued)

*Primary Examiner* — Matthew D Krcha
(74) *Attorney, Agent, or Firm* — Jones Robb, PLLC

(57) ABSTRACT

A biological analysis system is provided. The system comprises an interchangeable assembly configured to accommodate any one of a plurality of sample holders, each respective sample holder configured to receive a plurality of samples. The system also includes a control system configured to cycle the plurality of samples through a series of temperatures. The system further includes an optical system configured to detect fluorescent signals emitted from the plu- (Continued)

rality of samples. The optical system, in particular, can comprise a single field lens, an excitation source, an optical sensor, and a plurality of filter components. The excitation source can be one or more light emitting diodes. The field lends can be a bi-convex lens.

14 Claims, 19 Drawing Sheets

Related U.S. Application Data

(60) Provisional application No. 61/564,027, filed on Nov. 28, 2011, provisional application No. 61/541,371, filed on Sep. 30, 2011.

(52) U.S. Cl.
CPC ............ *B01L 7/52* (2013.01); *B01L 2200/023* (2013.01); *B01L 2200/025* (2013.01); *B01L 2200/028* (2013.01); *B01L 2200/143* (2013.01); *B01L 2300/021* (2013.01); *B01L 2300/046* (2013.01); *B01L 2300/0654* (2013.01); *B01L 2300/0829* (2013.01); *B01L 2300/1827* (2013.01); *B01L 2300/1844* (2013.01)

(56) References Cited

U.S. PATENT DOCUMENTS

| | | |
|---|---|---|
| 2002/0108380 A1 | 8/2002 | Nielsen et al. |
| 2003/0170883 A1 | 9/2003 | Martin et al. |
| 2004/0018610 A1 | 1/2004 | Sandell |
| 2004/0219074 A1* | 11/2004 | Childers ............... B01L 3/5085 422/534 |
| 2005/0151972 A1 | 7/2005 | Boege et al. |
| 2005/0279949 A1 | 12/2005 | Oldham et al. |
| 2006/0013736 A1 | 1/2006 | Blok et al. |
| 2006/0145098 A1 | 7/2006 | Baek et al. |
| 2006/0233670 A1 | 10/2006 | Lehto |
| 2007/0242105 A1* | 10/2007 | Srinivasan ................ B81B 1/00 347/63 |
| 2008/0000892 A1 | 1/2008 | Hirano |
| 2008/0038163 A1 | 2/2008 | Boege et al. |
| 2008/0163702 A1 | 7/2008 | Sunwoldt et al. |
| 2008/0176290 A1 | 7/2008 | Joseph et al. |
| 2008/0182301 A1* | 7/2008 | Handique ......... B01L 3/502723 435/91.2 |
| 2008/0268434 A1 | 10/2008 | Nurmi et al. |
| 2009/0214088 A1 | 8/2009 | Sorenson et al. |
| 2010/0129896 A1* | 5/2010 | Knapp .................... C12Q 1/686 435/285.1 |
| 2010/0248981 A1* | 9/2010 | Shirazi ............... G01N 35/0099 506/9 |
| 2011/0007955 A1* | 1/2011 | Ho ................... G06K 19/06028 382/128 |

FOREIGN PATENT DOCUMENTS

| | | |
|---|---|---|
| DE | 102005044021 | 3/2007 |
| EP | 0 640 828 A1 | 3/1995 |
| EP | 0 906 449 B1 | 3/2004 |
| EP | 1681555 A1 | 7/2006 |
| EP | 1764607 A1 | 3/2007 |
| JP | 2004-150808 A | 5/2004 |
| JP | 2005523009 A | 8/2005 |
| JP | 2005533500 A | 11/2005 |
| JP | 2006226998 A | 8/2006 |
| JP | 2006242726 A | 9/2006 |
| JP | 2006522330 A | 9/2006 |
| JP | 2007024537 A | 2/2007 |
| JP | 2008509398 A | 3/2008 |
| JP | 2008519266 A | 6/2008 |
| JP | 2009042226 A | 2/2009 |
| JP | 2010502228 A | 1/2010 |
| JP | 2010-516281 A | 5/2010 |
| WO | 9639481 A2 | 12/1996 |
| WO | 0184463 A2 | 11/2001 |
| WO | 0241999 A1 | 5/2002 |
| WO | 03029397 A1 | 4/2003 |
| WO | 03089136 A1 | 10/2003 |
| WO | 2004009239 A1 | 1/2004 |
| WO | 2004018105 A1 | 3/2004 |
| WO | 2004023117 A1 | 3/2004 |
| WO | 2006002226 A1 | 1/2006 |
| WO | 2006036307 A2 | 4/2006 |
| WO | 2007112114 A2 | 10/2007 |
| WO | 2008030914 A2 | 3/2008 |

OTHER PUBLICATIONS

Japanese Notification of Reasons for Refusal for Application No. JP 2014-533436, dated Jun. 30, 2016, with Machine English Translation.
Chinese First Search for Application No. CN 2012800585495, dated Apr. 23, 2015.
Chinese First Office Action for Application No. CN 2012800585495, dated May 4, 2015, with English Translation.
Notification of Reasons for Refusal issued in Japanese Patent Application No. 2017-00047, dated Jun. 25, 2018, with English machine translation.
Written Opinion and Search Report in Application No. 10201602113T, dated Dec. 26, 2017.
International Search Report and Written Opinion of the ISA for International Application No. PCT/US2012/058096, dated Jul. 8, 2013.
Notice of Reasons for Refusal issued in corresponding Japanese Application No. 2019-124325 dated Jul. 6, 2020.
JP Notification of Reason for Rejection issued in Japanese Application No. 2019-124325, dated Mar. 1, 2021.
JP Decision of Final Rejection issued in Japanese Application No. 2019-124325, dated Jul. 5, 2021.
JP Ruling of Declining Amendment issued in Japanese Application No. 2019-124325, dated Jul. 5, 2021.

* cited by examiner

SYSTEMS AND METHODS FOR BIOLOGICAL ANALYSIS

CROSS-REFERENCE TO RELATED APPLICATIONS

This application is a divisional of U.S. patent application Ser. No. 14/348,504, filed Mar. 28, 2014, which is a U.S. National Application filed under 35 U.S.C. § 371 of International Application No. PCT/US2012/058096, filed Sep. 28, 2012, which claims the benefit of priority of U.S. Provisional Application No. 61/564,027, filed on Nov. 28, 2011 and U.S. Provisional Application No. 61/541,371, filed on Sep. 30, 2011 each of which is incorporated herein by reference in its entirety.

FIELD OF THE INVENTION

The present invention relates generally to systems, devices, and methods for observing, testing, and/or analyzing one or more biological samples, and more specifically to systems, devices, and methods for observing, testing, and/or analyzing an array of biological samples.

DESCRIPTION OF THE RELATED ART

Generally, there is an increasing need to automate biological analysis systems to increase efficiency. For example, advances in automated biological sample processing instruments allow for quicker, more efficient, and high throughput analysis of samples. These types of systems may assay a greater number of samples than previous systems.

However, there is also an increasing need to provide biological analysis systems with greater flexibility to handle both low throughput and high throughput sample analyses while still providing a faster and more efficient automated system.

SUMMARY OF THE INVENTION

In an embodiment of the present invention, a biological analysis system is provided. The system comprises an interchangeable assembly configured to accommodate any one of a plurality of sample holders, each respective sample holder configured to receive a plurality of samples. The system also includes a control system configured to cycle the plurality of samples through a series of temperatures. The system further includes an optical system configured to detect fluorescent signals emitted from the plurality of samples. The optical system, in particular, can comprise a single field lens, an excitation source, an optical sensor, and a plurality of filter components. The excitation source can be one or more light emitting diodes. The field lens can be a bi-convex lens.

In another embodiment, the plurality of sample holders can include, for example, a 96-well block, a 384-well block, a low-density array, or a through-hole array. In an alternative embodiment, the sample holder is a through-hole array. The through-hole array can comprise 48 locations, each location including a subarray having dimensions of 8 through holes by 8 through holes.

In yet another embodiment, the optical system can be further configured to confirm that the sample holder is properly positioned on the interchangeable assembly.

In a further embodiment, the sample holder can further include an identifier that references a data file storing data related to the sample holder. The optical system can be further configured to image the identifier to confirm that the correct sample holder is positioned on the interchangeable assembly.

In yet a further embodiment, the biological system can further include a temperature control system configured to maintain the excitation source within a defined temperature range. The temperature control system can comprise a fan configured to operate intermittently to maintain the excitation source within a defined temperature range.

In an embodiment of the present invention, a biological analysis system is provided. The system comprises a thermal cycler. The thermal cycler includes a block assembly, an optical system, a user interface, and a processor. The block assembly can be configured to receive a plurality of samples and cycle the plurality of samples through a series of temperatures. The optical system can comprise an optical sensor configured to detect a fluorescence level emitted from each of the plurality of samples. The user interface can be integrated on an exterior surface thermal cycler device. The processor can be programmed to process the detected fluorescence levels and display the fluorescence levels on the integrated user interface in real-time, wherein the parameters for displaying fluorescent levels are changeable based on user preference.

In another embodiment, the parameters can be, for example, a selection of one or more sample holders that receive the plurality of samples, a selection one or more wells within the one or more sample holders, a selection of one or more dyes within the one or more wells, or combinations thereof. The one or more sample holders can include, for example, a 96-well block, a 384-well block, a low-density array, and a through-hole array.

In yet another embodiment, the processor can be programmed to display the fluorescence levels in the form of real-time amplification plots.

In a further embodiment, the block assembly is an interchangeable block assembly which can accommodate any one of a 96-well block, a 384-well block, a low-density array, and a through-hole array, wherein the processor is programmed to display the fluorescence levels in the form of real-time amplification plots for any one of the plurality of sample holders.

In an embodiment of the present invention, a biological analysis system is provided. The system includes a block assembly configured to accommodate one or more cases, wherein each case is configured accommodate a sample holder that receives a plurality of samples. The system also includes a cover comprising. The cover can have a frame having a contact surface, a platen, a sealing material and a heat source. The sealing material can be configured to contact the block assembly to form an enclosed volume of air between the sample holders and the platen. The heat source can be configured to heat the enclosed volume of air to prevent (a) condensation on the one or more cases and (b) thermal non-uniformity of the sample holders when the sample holders are cycled through a series of temperatures.

In another embodiment, the sealing material is a gasket formed to the contact surface of the frame. The gasket can be configured and arranged to contact the block assembly and not contact the sample holders.

In yet another embodiment, the block assembly can further include a carrier shaped to accommodate the one or more cases, wherein the sealing material is arranged to form to the carrier.

In a further embodiment, the one or more cases can include a thermally conductive material. The thermally conductive material is selected from the group consisting of aluminum, graphite, zinc, berilum, stainless steel, and combinations thereof.

In yet a further embodiment, the platen can include one or more transparent plates each positioned directly above a corresponding sample holder. One of the transparent plates can have substantially the same dimensions as the corresponding sample holder. The transparent plates can also positioned at an angle relative to the sample holder to prevent reflection of light passing through the one or more transparent plates. Further, the transparent plates can be glass plates.

In an embodiment of the present invention, a biological analysis system is provided. The system includes a block assembly configured to accommodate one or more cases, wherein each case is configured accommodate a sample holder that receives a plurality of samples. The system also includes a data file and a fill station. The data file has instructions for arranging the plurality of samples onto a plurality of sample locations on the one or more sample holders. The instructions can be, for example, sample loading instructions, assay definitions for each sample, sample location definitions, or combinations thereof.

The fill station can include a processor configured to execute the instructions, wherein the fill station is configured to load each sample holder with a plurality of samples according to the executed instructions. The processor can be further configured to modify the received data file with information selected from the group consisting of updated sample locations, updated positional locations, and combinations thereof.

In another embodiment, each of the cases is constructed and arranged to accept a case cover to enclose each of the loaded sample holders and provide a sealed interior within each case and corresponding case cover. Each case or each corresponding case cover can be configured to receive a liquid that is immiscible with the samples into the sealed interior. The immiscible liquid can be a perfluorinated hydrocarbon, a hydrocarbon, an oil, or a silicone fluid.

In yet another embodiment, the system further includes an automated device for transferring loaded sample holders from the fill station to the block assembly.

In a further embodiment, at least one sample holder comprises an identifier, which can be a barcode.

In an embodiment of the present invention, a biological analysis system is provided. The system includes a block assembly, a data file that stores instructions, an optical system and a processor. The block assembly can be configured to accommodate one or more sample holders loaded with a plurality of samples, wherein the sample holders includes an identifier. The identifier can be a barcode. The optical system can be configured to (a) detect fluorescent signals emitted from the plurality of samples and (b) image the identifier to identify the data file and identify the sample holder.

In an embodiment, processor executes instructions of the identified data file to cycle the plurality of samples though a series of temperatures. The instructions can be, for example, sample loading instructions, assay definitions for each sample, sample location definitions, or combinations thereof.

Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION

The following description provides embodiments of the present invention, which are generally directed to systems, devices, and methods for preparing, observing, testing, and/or analyzing an array of biological samples. Such description is not intended to limit the scope of the present invention, but merely to provide a description of embodiments.

Exemplary systems, methods and devices related to the various embodiments described in this document include those described in U.S. Provisional Patent Application No. 61/541,453, U.S. Provisional Patent Application No. 61/541,342, U.S. Provisional patent application Ser. No. 29/403,049, U.S. Provisional Patent Application No. 61/541,495, and U.S. Provisional Patent Application No. 61/541,366, all of which were filed Sep. 30, 2011, and all of which are also incorporated herein in their entirety by reference.

System Overview

Figure 1:
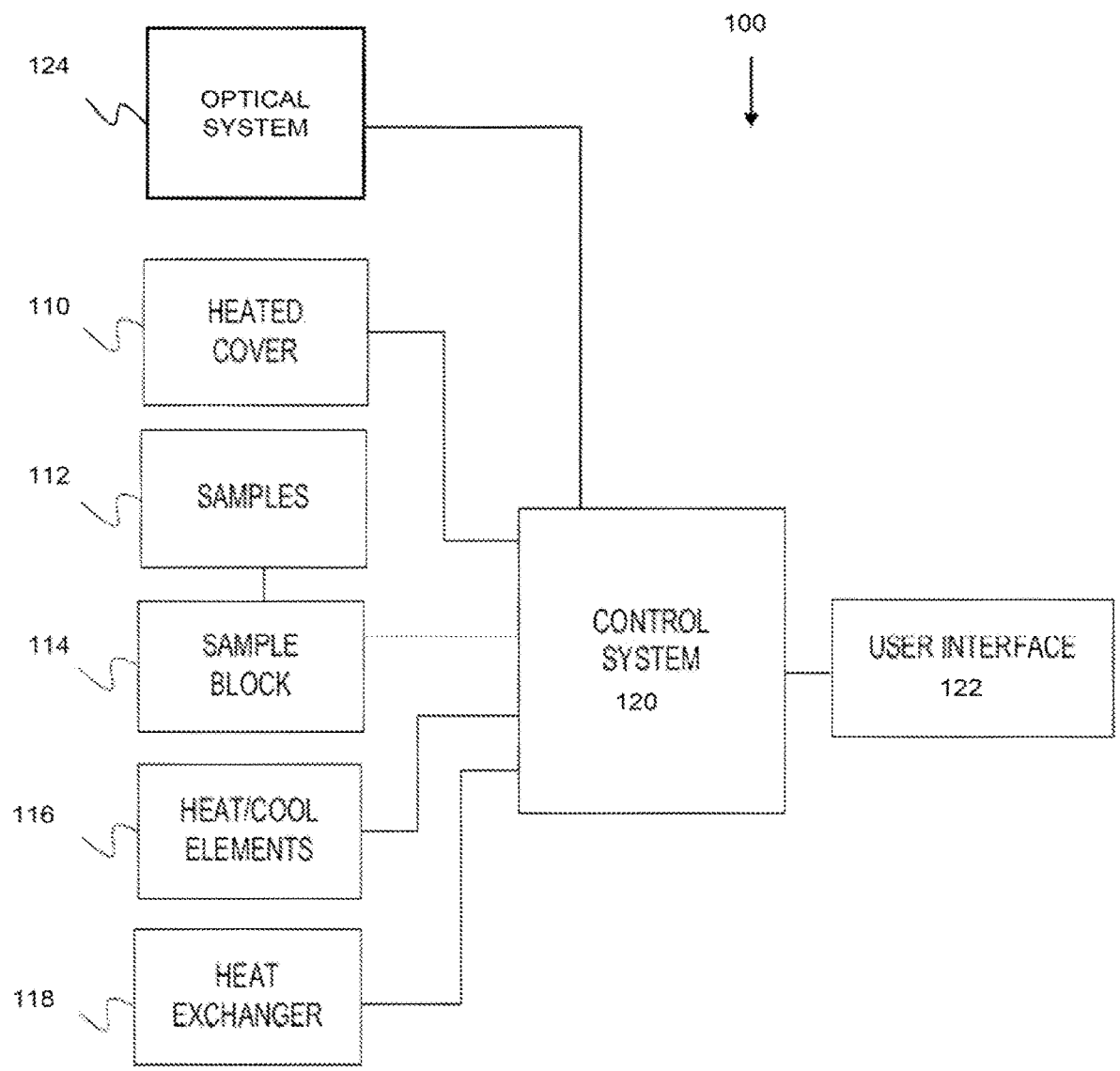
FIG. 1 is a block diagram that illustrates an exemplary instrument, upon which embodiments of the present teachings may be implemented.

To prepare, observe, test, and/or analyze an array of biological samples, one example of an instrument that may be utilized according to various embodiments is a thermal cycler device, such as an end-point polymerase chain reaction (PCR) instrument or a quantitative, or real-time, PCR instrument. FIG. 1 is a block diagram that illustrates a thermal cycler 100, upon which embodiments of the present teachings may be implemented. Thermal cycler 100 may include a heated cover 110, discussed in greater detail below, which is placed over a sample block 114 loaded with a plurality of samples 112 contained in a sample holder (not shown), also discussed in greater detail below.

In various embodiments, the sample holder may have a plurality of sample regions, or wells, configured for receiving a plurality of samples, wherein the wells may be sealed within the sample holder via a lid, cap, sealing film or any other sealing mechanism between the wells and heated cover 110. Some examples of a sample holder may include, but are not limited to, any size multi-well plate, card or array including, but not limited to, a 24-well microtiter plate, 48-well microtiter plate, a 96-well microtiter plate, a 384-well microtiter plate, a microcard, a through-hole array, or a substantially planar holder, such as a glass or plastic slide. The wells in various embodiments of a sample holder may include depressions, indentations, ridges, and combinations thereof, patterned in regular or irregular arrays formed on the surface of the sample holder substrate. Sample or reaction volumes can also be located within wells or indentations formed in a substrate, spots of solution distributed on the surface a substrate, or other types of reaction chambers or formats, such as samples or solutions located within test sites or volumes of a microfluidic system, or within or on small beads or spheres.

In another embodiment, an initial sample or solution may be divided into hundreds, thousands, tens of thousands, hundreds of thousands, or even millions of reaction sites, each having a volume of, for example, a few nanoliters, about one nanoliter, or less than one nanoliter (e.g., 10's or 100's of picoliters or less).

Thermal cycler 100 may also include a sample block 114, elements for heating and cooling 116, a heat exchanger 118, a control system 120, and a user interface 122, wherein components 114, 116 and 118 can be included within a thermal block assembly. The thermal block assembly can have an interchangeable feature such that thermal block assembly can be configured to accommodate any one of the multiple sample holders, and their associated sample blocks, stated above.

In an embodiment, the elements for heating and cooling 116 can be thermoelectric devices such as, for example, Peltier devices. The number of thermoelectric devices used within a thermal block assembly can depend on a number of factors including, but not limited to, cost, the number of independent zones desired, and the size of the sample holder. For example, a sample block for holding a 48-well microtiter plate may be sized to accommodate a single thermoelectric device, whereas sample blocks configured for plates having more wells may accommodate more than one thermoelectric device such as, for example, four thermoelectric devices. Moreover, if control over multiple zones on a sample block is desired, the number of thermoelectric devices can vary from a single thermoelectric device to, for example, a thermoelectric device per sample region (e.g., well, through-hole, reaction site, etc.) on the sample block.

In an alternative embodiment, thermal cycler 100 can have a two-sided thermal assembly, where elements for heating and cooling 116 and heat exchanger 118 can be provided above (upper side) and below (lower side) sample block 114 and associated samples 112. In such an embodiment, the upper side of the two-sided thermal assembly provided above sample block 114 and associated samples 112, can replace heater cover 110 above samples 112. Such a configuration could provide more uniform heating from above and below the samples. For a real-time thermal cycler, the upper side can have portions of clear construction to allow for the passing of an excitation light source and emitted fluorescence. Such portions can be made of any clear material including, for example, plastic and glass.

Thermal cycler 100 can also have an optical system 124. In FIG. 1, optical system 124 may have an illumination source (not shown) that emits electromagnetic energy, an optical sensor, detector, or imager (not shown), for receiving electromagnetic energy from samples 112 in a sample holder, and optics used to guide the electromagnetic energy from each DNA sample to the imager. The optical system is discussed in more detail below.

Control system 120 may be used to control the functions of optical system 124, heated cover 110, and the thermal block assembly, which can comprise sample block 114, heating and cooling elements 116, and heat exchanger 118. Control system 120 may be accessible to an end user through user interface 122 of thermal cycler 100 in FIG. 1.

Figure 2:
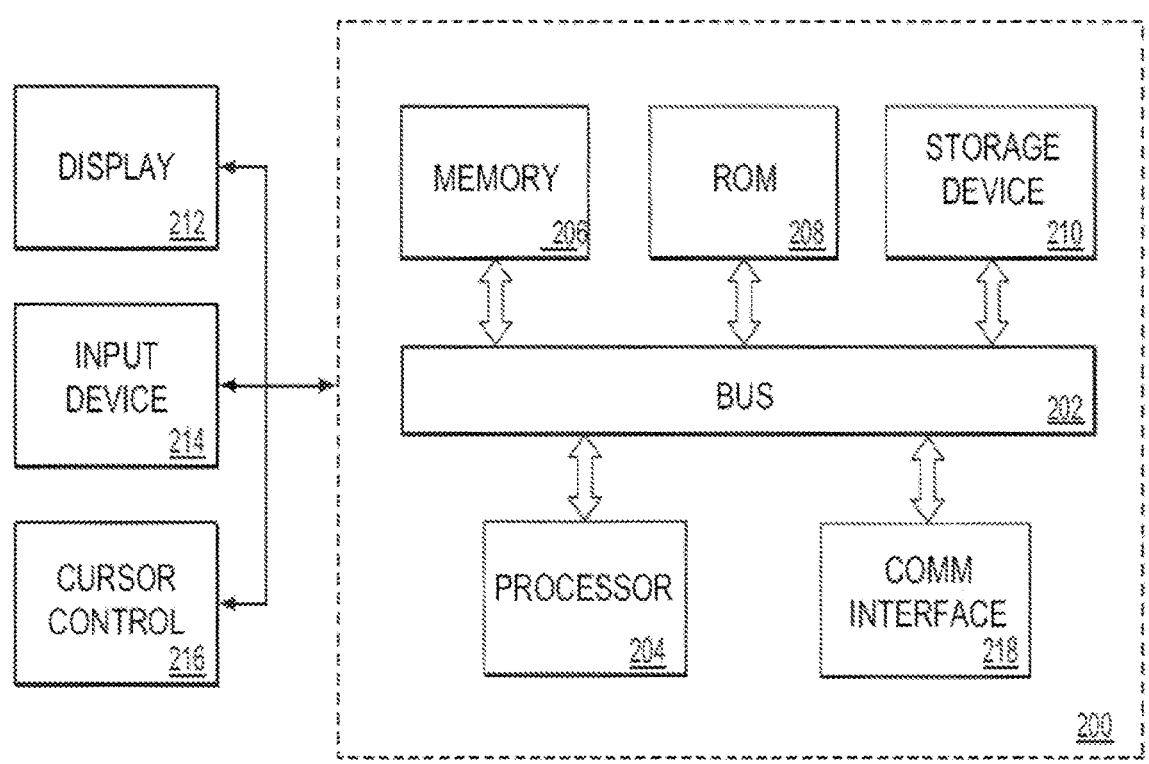
FIG. 2 is a block diagram that illustrates a computer system, upon which embodiments of the present teachings may be implemented.

Referring to FIG. 2, a computer system 200 may provide control to the function of thermal cycler 100 in FIG. 1, as well as the user interface function. Additionally, computer system 200 of FIG. 2 may provide data processing, display and report preparation functions. All such instrument control functions may be dedicated locally to the PCR instrument. As such, computer system 200 can serve as control system 120 illustrated in FIG. 1. Computer system 200 of FIG. 2 may also provide remote control of part or all of the control, analysis, and reporting functions, as will be discussed in more detail subsequently.

In an alternative embodiment, computer system 200 may serve as a control system between thermal cycler 100 and other thermal cyclers that may be responsive to instructions sent by computer system 200 on thermal cycler 100. For example, thermal cycler 100 can be a real-time thermal cycler, while the other thermal cyclers are end-point thermal cyclers. For high-throughput genotyping needs, for example, a user can thermal cycle multiple through-hole plates on end-point thermal cyclers electrically connected to real-time thermal cycler 100, then followed by a short final detection on real-time thermal cycler 100. With a built-in capability of communication capability of computer system 200 (discussed below), the thermal cycle conditions on the end-point thermal cyclers can be dynamically adjusted to increase the throughput without sacrificing the performance. One way to achieve this would be to run a control plate on real-time thermal cycler 100. With the real-time fluorescence data from real-time thermal cycler 100, an algorithm can be run in real-time to determine the genotyping performance. As soon as the desired performance is achieved with confidence on real-time thermal cycler 100, the thermal cycle conditions can be distributed, via computer system 200, to adjust or stop the runs on the electrically connected end-point thermal cyclers. The benefit will be reduced thermal cycle time on the end-point thermal cyclers, and therefore increased throughput capability.

In particular reference to FIG. 2, computing system 200 can include one or more processors, such as a processor 204. Processor 204 can be implemented using a general or special purpose processing engine such as, for example, a microprocessor, controller or other control logic. Processor 204 can therefore be connected to a bus 202 or other communication medium for communicating information.

Computing system 200 of FIG. 2 may also be embodied in any of a number of forms, such as a rack-mounted computer, mainframe, supercomputer, server, client, a desktop computer, a laptop computer, a tablet computer, handheld computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 200 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 200 may be configured to connect to one or more servers in a distributed network. Computing system 200 may receive information or updates from the distributed network. Computing system 200 may also transmit information to be stored within the distributed network that may be accessed by other clients connected to the distributed network.

Computing system 200 of FIG. 2 also includes a memory 206, which can be a random access memory (RAM) or other dynamic memory, coupled to bus 202 for storing instructions to be executed by processor 204. Memory 206 also may be used for storing temporary variables or other intermediate information during execution of instructions to be executed by processor 204.

Computing system 200 further includes a read only memory (ROM) 208 or other static storage device coupled to bus 202 for storing static information and instructions for processor 204.

Computing system 200 may also include a storage device 210, such as a magnetic disk, optical disk, or solid state drive (SSD) is provided and coupled to bus 202 for storing information and instructions. Storage device 210 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having particular computer software, instructions, or data stored therein.

In alternative embodiments, storage device 210 may include other similar instrumentalities for allowing computer programs or other instructions or data to be loaded into computing system 200. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 210 to computing system 200.

Computing system 200 of FIG. 2 can also include a communications interface 218. Communications interface 218 can be used to allow software and data to be transferred between computing system 200 and external devices. Examples of communications interface 218 can include a modem, a network interface (such as an Ethernet or other NIC card), a communications port (such as for example, a USB port, a RS-232C serial port), a PCMCIA slot and card, Bluetooth, etc. Software and data transferred via communications interface 218 are in the form of signals which can be electronic, electromagnetic, optical or other signals capable of being received by communications interface 218. These signals may be transmitted and received by communications interface 218 via a channel such as a wireless medium, wire or cable, fiber optics, or other communications medium. Some examples of a channel include a phone line, a cellular phone link, an RF link, a network interface, a local or wide area network, and other communications channels.

Computing system 200 may be coupled via bus 202 to a display 212, such as a cathode ray tube (CRT) or liquid crystal display (LCD), for displaying information to a computer user. An input device 214, including alphanumeric and other keys, is coupled to bus 202 for communicating information and command selections to processor 204, for example. An input device may also be a display, such as an LCD display, configured with touchscreen input capabilities. Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (e.g., x) and a second axis (e.g., y), that allows the device to specify positions in a plane. A computing system 200 provides data processing and provides a level of confidence for such data. Consistent with certain implementations of embodiments of the present teachings, data processing and confidence values are provided by computing system 200 in response to processor 204 executing one or more sequences of one or more instructions contained in memory 206. Such instructions may be read into memory 206 from another computer-readable medium, such as storage device 210. Execution of the sequences of instructions contained in memory 206 causes processor 204 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 204 for execution. Such instructions, generally referred to as "computer program code" (which may be grouped in the form of computer programs or other groupings), when executed, enable the computing system 200 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 210. Volatile media includes dynamic memory, such as memory 206. Transmission media includes coaxial cables, copper wire, and fiber optics, including the wires that comprise bus 202.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 204 for execution. For example, the instructions may initially be carried on magnetic disk of a remote computer. The remote computer can load the instructions into its dynamic memory and send the instructions over a telephone line using a modem. A modem local to computing system 200 can receive the data on the telephone line and use an infra-red transmitter to convert the data to an infra-red signal. An infra-red detector coupled to bus 202 can receive the data carried in the infra-red signal and place the data on bus 202. Bus 202 carries the data to memory 206, from which processor 204 retrieves and executes the instructions. The instructions received by memory 206 may optionally be stored on storage device 210 either before or after execution by processor 204.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Optical System Design

As summarized above and illustrated in FIG. 1, thermal cycler 100 can include optical system 124.

Figure 3:
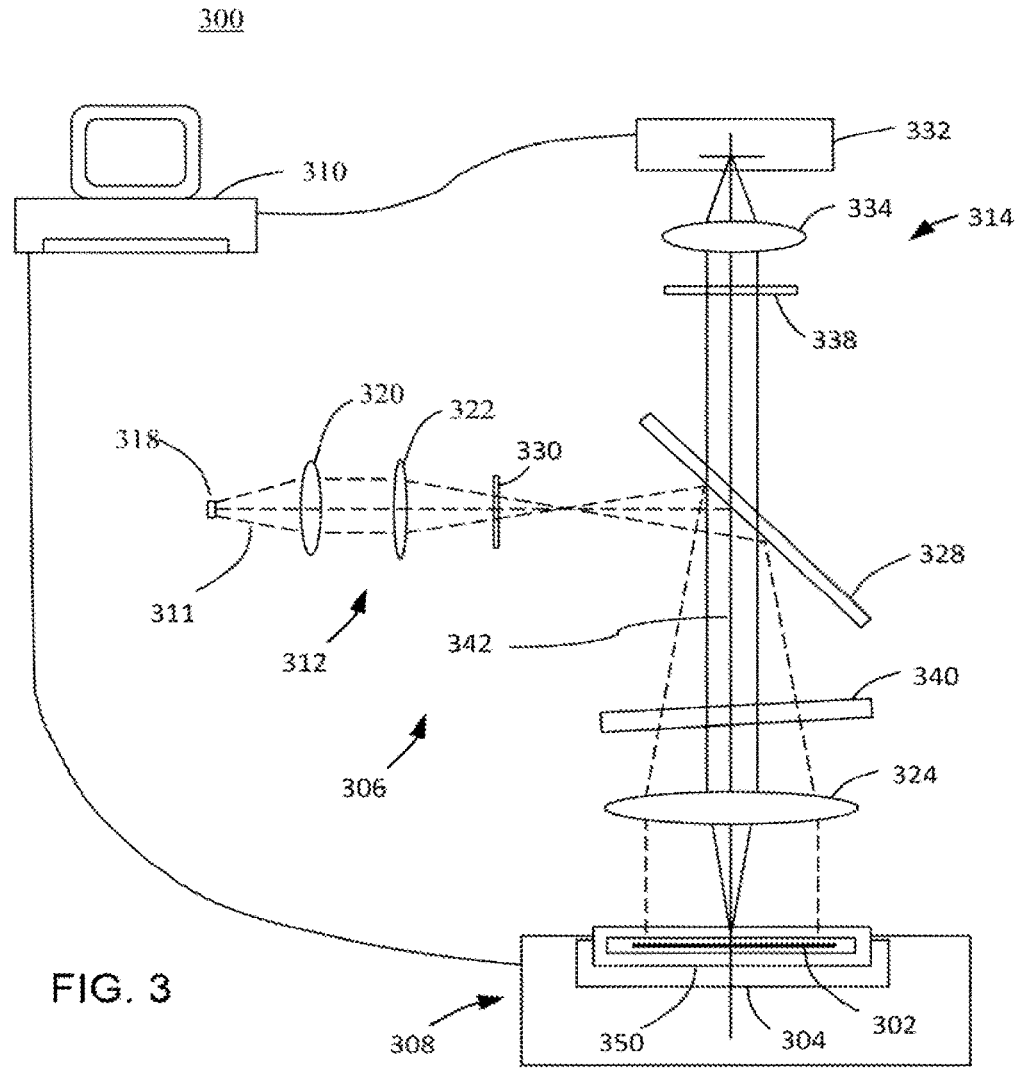
FIG. 3 is a system for processing biological samples according to embodiments of the present invention.

FIG. 3 illustrates certain components of an optical system for monitoring and/or measuring one or more biological processes of the biological samples. In the illustrated embodiment of FIG. 3, a system 300 is provided with a sample holder 302, wherein system 300 and holder 302 may be suitable, for example, for performing real-time PCR processes on a plurality of biological samples and performing other biological or biochemistry processes such as sequencing or genotyping measurements.

In certain embodiments, sample holder 302 is disposed within an enclosure or case 350 that may be sealed, for example, to reduce or prevent evaporation of the biological samples. Moreover, one or more sample holders 302 or sample cases 350 can be retained, located and/or supported by carrier 304 configured for aligning and/or transporting the sample holder 302 within system 300.

In the embodiment of FIG. 3, an optical system 306 is provided, which comprises an excitation system 312 for illuminating sample holder 302 and the associated biological samples, and an emission optical system 314 for receiving emissions from the biological samples, for example, due to fluorescent signals produced by one or more fluorescent dyes or probe molecules present in the biological samples and in response to an excitation beam.

Excitation optical system 312 may include an excitation source 318, lenses 320, 322, 324, and a beamsplitter 328. Excitation optical system 312 may also include one or more optical filters 330 for limiting the wavelength range of light received by the biological samples. The excitation source can be, for example, one or more light emitting diodes (LEDs), a halogen lamp, or any other light source capable of illuminating the biological samples being tested for the purpose of detecting the fluorescence emitted therefrom.

Emission optical system 314 may include optical sensor 332, lenses 324, 334, and beamsplitter 328. Emission optical system 314 may also include one or more optical filters 338 for limiting the wavelength range of light received by optical sensor 332.

In certain embodiments, the combination of lenses or lens systems 324, 334 is selected to provide a predetermined optical result or image quality. For example, in order to reduce system cost or to simplify the emission optical system 314 design, lens 334 may comprise a commercially available camera lens. Such lenses can provide very high image quality (e.g., images with low chromatic and monochromatic aberration) under certain viewing conditions. However, the careful balance of higher order aberrations incorporated into such camera lens design used to provide such high image quality can be disturbed with the introduction of other lenses into an imaging system. For example, in the illustrated embodiment shown in FIG. 3, a field lens such as lens 324 is added to emission optical system 314. Lens 324 is common to both excitation optical system 312 and emission optical system 314 to provide both a generally more compact optical system and efficient transfer of fluorescent energy from a sample to the detection system.

In addition, optical system 306 may include one or more windows 340 configured to isolate portions of system 300, for example, to reduce or eliminate unwanted thermal or optical effects during processing of the biological samples.

Windows 340 may be disposed parallel to a surface of sample holder 302 and/or perpendicular to optical axis 342. Alternatively, windows 340 may be disposed at an angle relative to a surface of sample holder 302 and/or at an acute angle to optical axis 342, for example, to reduce retro-reflections of light from excitation beam 311 back toward optical sensor 332. Windows 340 may also include an antireflective coating to reduce retro-reflections of light from excitation beam 311 back toward optical sensor 332. The antireflective coating may be used in addition to, or as an alternative to, tilting windows 340.

Optical system 306 can also include a temperature control system configured to maintain excitation source 318 within a defined temperature range. In an embodiment, the temperature control system is a fan with controller configured to operate the fan intermittently to maintain the excitation source within a defined temperature range, thereby preventing spectral shift and intensity variations from the excitation source. By operating the fan intermittently, or pulsing the fan, the processor prevents the excitation source temperature from being too close to ambient and therefore difficult to control. On the other hand, intermittent fan operation also prevents the excitation source temperature from getting too hot and, as a consequence, shortening the life of the excitation source.

As stated above with reference to FIG. 1, the thermal block assembly can have an interchangeable feature such that the thermal block assembly can be configured to accommodate any one of multiple sample blocks 114 and, as a result, sample holders including, for example, a standard microtiter 96-well, a 384-well plate, a microcard (a low-density array), a through-hole array (a high-density array), or a substantially planar holder, such as a glass or plastic slide.

Generally, to accomplish such interchangeability in a single system, a combination of field lenses would be necessary to accommodate such variances in sample volumes associated with the different examples of sample holders, particularly considering the flexibility required to accommodate the variance in design and well volume between a through-hole high density array and any other type of sample holder. It has surprisingly been discovered, however, that such flexibility can be attained using a single field lens 324 (see FIG. 3). In an embodiment, the single field lens can be a custom bi-convex lens.

Figure 4:
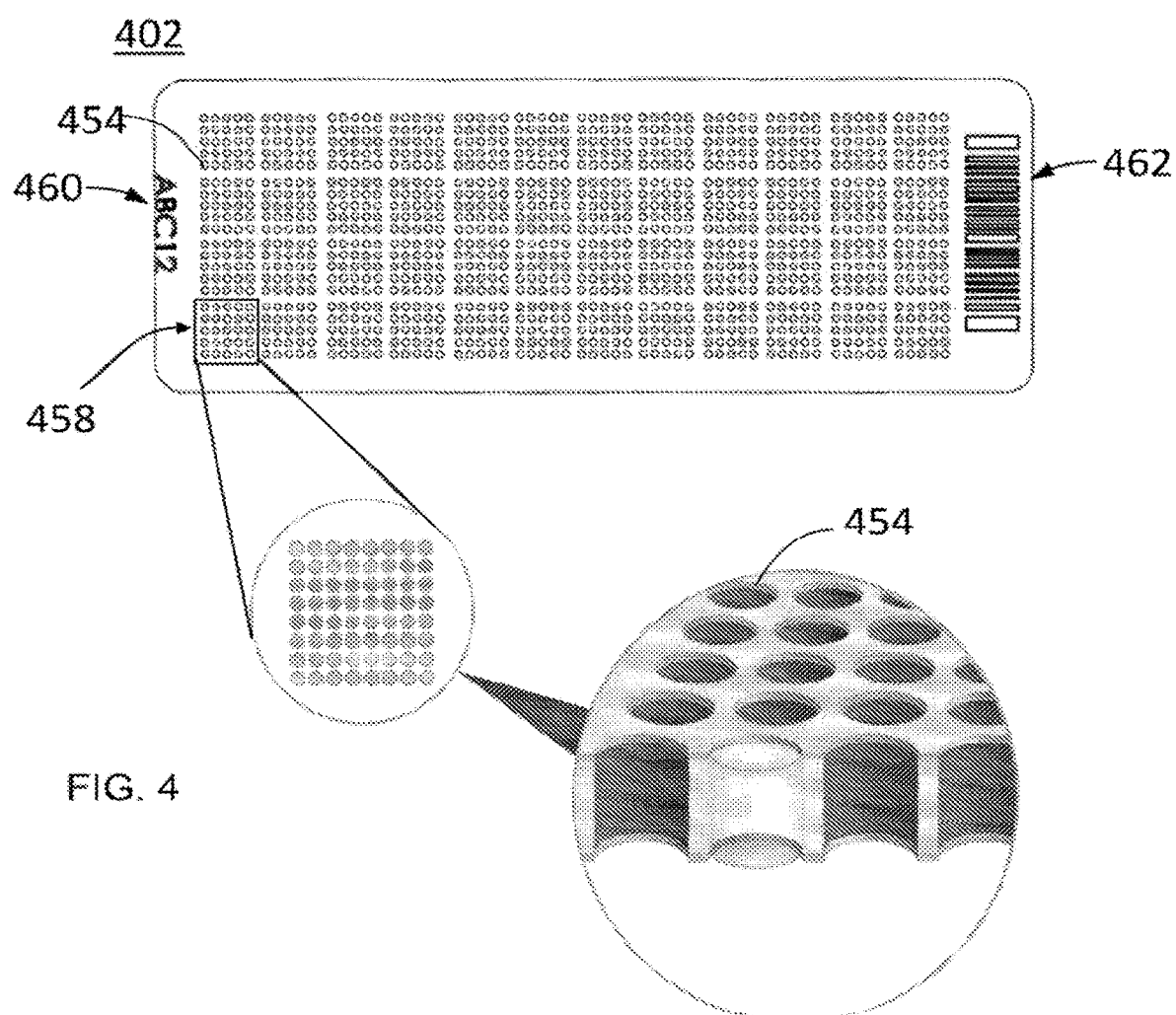
FIG. 4 is a sample holder according to an embodiment of the present invention.

Regarding through-hole arrays, FIG. 4 illustrates a sample holder 402 including a planar substrate comprising a plurality of through-holes 454. In certain embodiments, through-holes 454 are evenly spaced from one another along a two-dimensional array. Alternatively, through-holes 454 may be grouped in a plurality of subarrays 458, for example, to facilitate loading of samples into different groups of through-holes 454. For example, in the illustrated embodiment shown in FIG. 4, sample holder 402 has dimensions of 4 by 12 subarrays, where each subarray can have dimensions of 8 by 8 individual through-holes 454, for a total of 3072 through-holes 454 on sample holder 402. Through-holes 454 may be dimensioned such that a liquid containing a biological sample and/or reference dye is held within through-holes 454 by surface tension or capillary forces, as illustrated in the magnified view of FIG. 4. This effect may be enhanced by coating the walls of through-holes 454 with a hydrophilic coating. In certain embodiments, the outer surfaces of sample holder 402 comprise a hydrophobic material or coating configured to reduce or eliminate cross-contamination or mixing between the samples located in the various through-holes 454. Various aspects and advantages of a through-hole arrangement for supporting biological samples are further disclosed in U.S. Pat. Nos. 6,306,578; 6,893,877; 7,682,565, the entire contents of each of which patents are hereby incorporated by reference in their entirety for all purposes as if fully set forth herein.

The sample holder 402 of FIG. 4 may also comprise alphanumeric characters 460, a barcode 462, or other identifier from which information relative to an individual holder 402 may be derived or ascertained. Such information includes, but is not limited to, reagents contained with some or all of the through-holes 454 and/or protocols to be followed when using sample holder 402, assay definitions, sample locations, positional mapping, or combinations thereof.

In certain embodiments, emission optical system 314 (see FIG. 3) is configured so that optical sensor 332 (see FIG. 3) may be used to read characters 460 and/or barcode 462. In addition, emission optical system 314 may be configured to provide images that contain, in a single frame, portions of one or more sample holders 402 containing through-holes 454 and either, or both, alphanumeric characters 460 or barcode 462 for each imaged sample holder.

Moreover, such images can also be used to confirm that the one or more sample holders are properly positioned in the block assembly. This confirmation is of importance for many reasons that include, for example, changing a sample holder to and from a through-hole high density array.

User Interface Features

As summarized above and illustrated in FIG. 1, thermal cycler 100 can include user interface 122. The user interface can be integrated on an exterior surface of thermal cycler 100. As also summarized above in FIG. 1, thermal cycler 100 can include control system 120, which may be used to control the functions of the detection system, heated cover, and thermal block assembly. Control system 120 may be accessible to an end user through the user interface 122 of thermal cycler 100. An example of a home screen on user interface 122 is provided in FIG. 5.

User interface 122 can simply be a cathode ray tube (CRT) or liquid crystal display (LCD), for displaying information to a computer user with a separate input device for communicating information and command selections to a processor on control system 120. The input device can include alphanumeric and other keys, for example. The input device can also include cursor control, such as a mouse, a trackball or cursor direction keys for communicating direction information and command selections to the processor and for controlling cursor movement on the interface.

Figure 5:
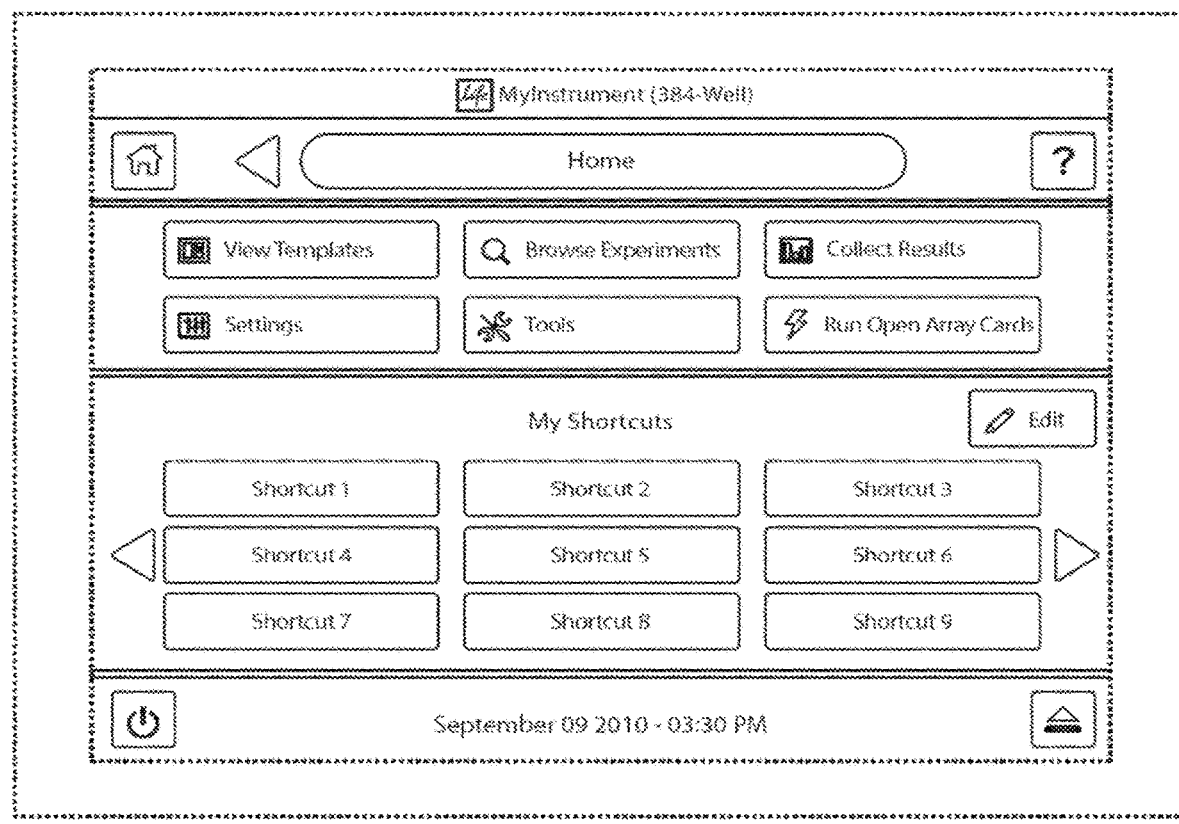
FIG. 5 is a home screen shot on a user interface according to an embodiment of the present invention.

In another embodiment, such as that illustrated in FIG. 5, user interface 122 can also be a display, such as an LCD display, configured with touchscreen input capabilities. It should be recognized that a display configured with touchscreen input capabilities may be used by the user to select functions, input text or characters via a touchscreen keyboard, or manipulate data and data views, for example.

Figure 6:
FIG. 6 is an experimental view screen shot on a user interface according to an embodiment of the present invention.
Figure 7:
FIG. 7 is a time view screen shot on a user interface according to an embodiment of the present invention.

Referring to FIG. 6, as an experiment is running on test samples, user interface can provide a touchscreen with a multi-tab view that allows a user to select from multiple possible views. In FIG. 6, for example, the user can select from an Experiment View, Time View and Plot View. FIG. 6 illustrates the Experiment View, while FIG. 7 illustrates the Time View and FIG. 8 illustrates the Plot View.

Using the fluorescence level emitted from test samples and detected on an optical sensor of the optical system, control system 120 (or computer system 200) can have processor 204 programmed to process, for example, the detected fluorescence levels and display the fluorescence levels on integrated user interface 122 in real-time, wherein the parameters for displaying fluorescent levels are changeable based on user preference.

These changeable/selectable parameters for displaying fluorescent levels can include, for example, selection of one or more sample holders that receive the multiple samples, a selection of one or more wells within the one or more sample holders, a selection of one or more dyes within the one or more wells, or combinations thereof. When a user selects from one or more sample holders to receive the multiple samples, the user can select from multiple sample holders, and corresponding sample blocks, that includes, for example, a 96-well block, a 384-well block, a low-density array, and a through-hole array.

Figure 8:
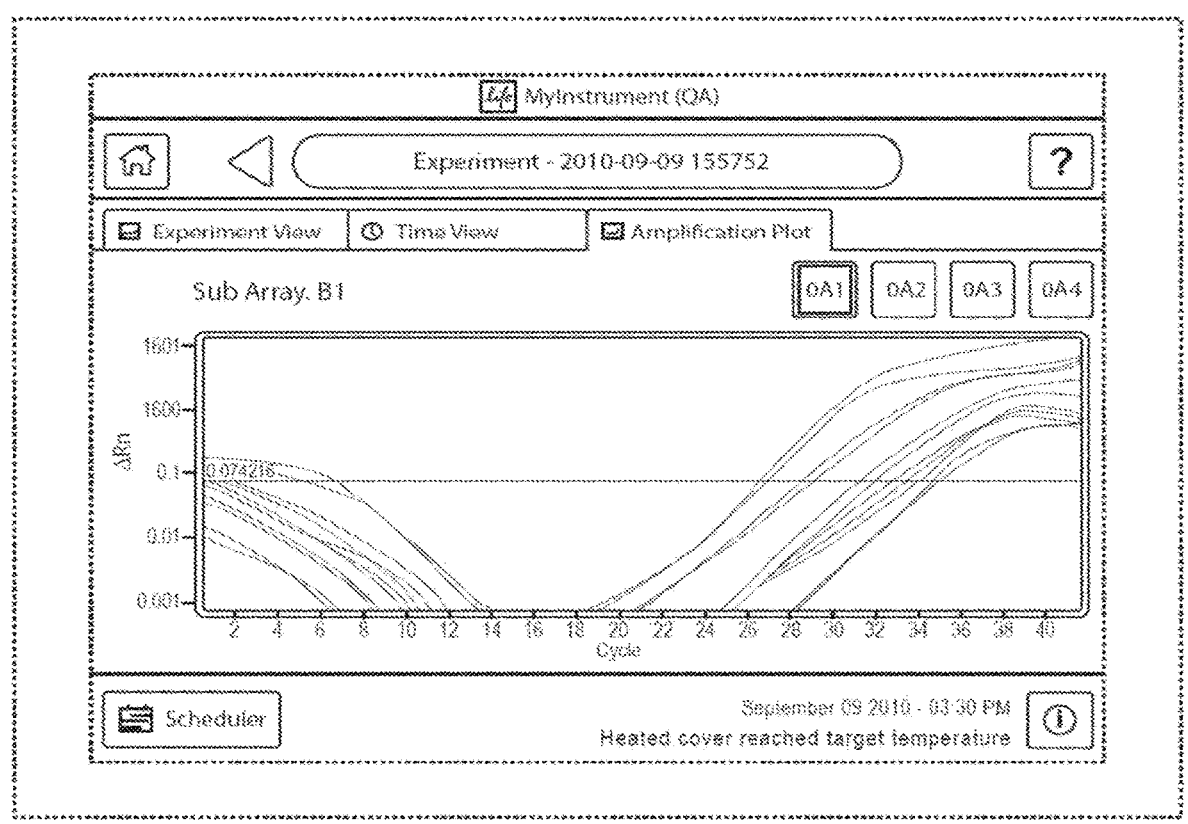
FIG. 8 is a plot screen shot on a user interface according to an embodiment of the present invention.

In an embodiment, processor 204 can be programmed to display the fluorescence levels in the form of real-time amplification plots as illustrated, for example, by the Plot View screen of FIG. 8. As mentioned previously, a display configured with touchscreen input capabilities may be used by a user to manipulate data and data views. For example, a user may be able to select a amplification curve of a specific sample to view by touching the desired amplification curve in the amplification plot. In another example, the user may zoom in on the data in the amplification plot by touching the display in a way that indicates a zoom command. Furthermore, other plots that may be displayed on user interface 122 are 3-D visualizations of the data. In these examples, a display configured with touchscreen input capabilities may be used to change the perspective views in a 3-D plot so that a user may visualize the data in another way that may provide more information.

Heated Cover Design

As summarized above and illustrated in FIG. 1, thermal cycler 100 can include heated cover 110.

Figure 9A:
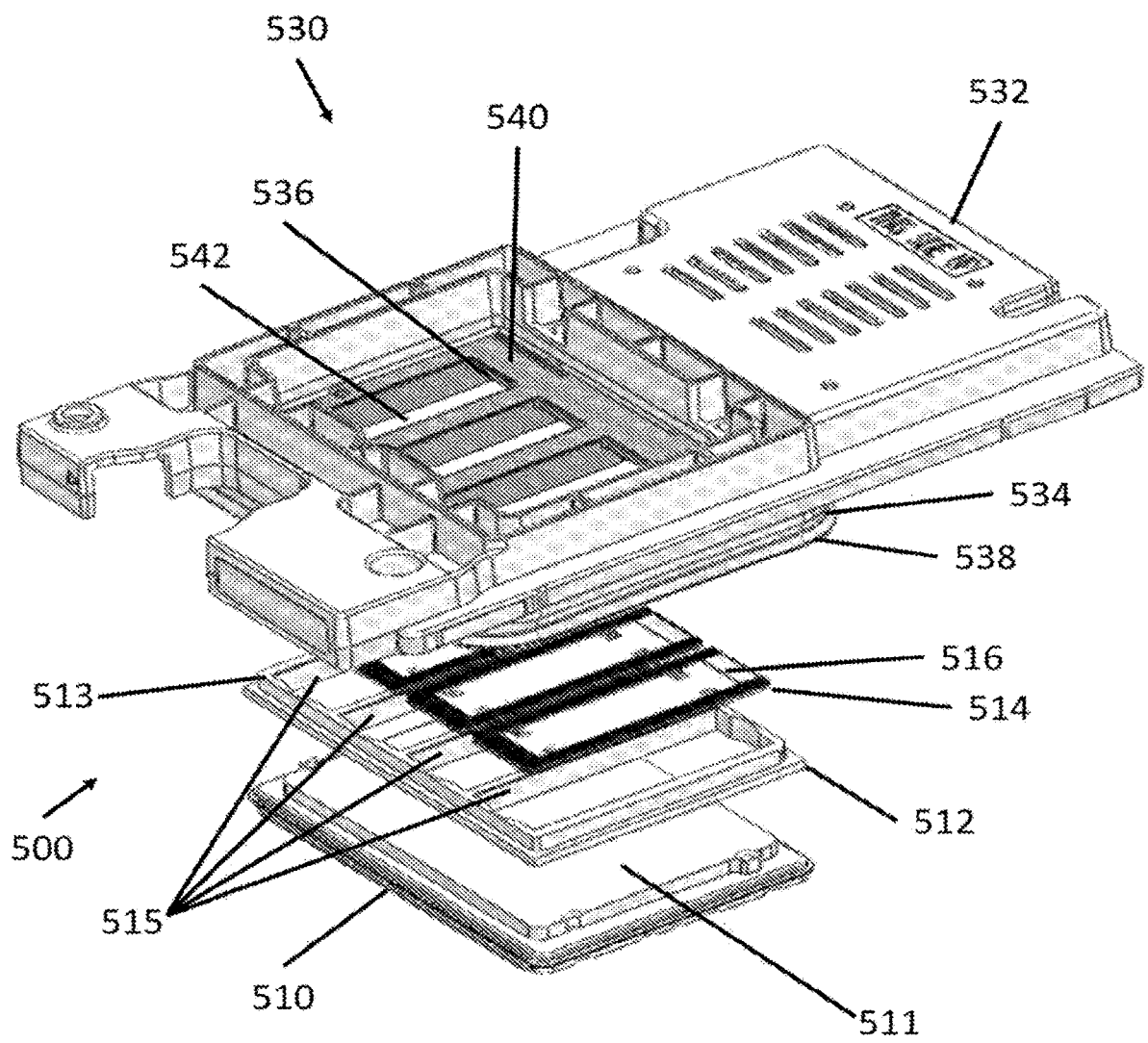
FIG. 9A is an exploded perspective view of a block assembly and heated cover according to an embodiment of the present invention.

Referring to FIG. 9A, a system 500 is provided that includes a block assembly 510 and a heater cover 530. Block assembly 510 can be configured to accommodate one or more sample holders 516. In another embodiment, block assembly 510 can be configured to accommodate one or more cases 514, each configured to accommodate one or more sample holders 516 that receives a plurality of samples. Cases 514 can include a thermally conductive material such as, for example, aluminum, graphite, zinc, beryllium, stainless steel, or combinations thereof.

In another embodiment, block assembly 510 can be configured to receive a carrier 512, which can accommodate one or more cases 514, each configured accommodate a sample holder 516 that receives a plurality of samples. This embodiment is illustrated in FIG. 9A. Carrier 512 can be molded, extruded, or machined by any similar means. Carrier 512 can be injection molded. Carrier 512 can comprise a polymer or plastic. The polymer can be non-fluorescing. The polymer can include polyphenylene sulfide and/or any other similar organic polymer.

Heated cover 530 can include a frame 532 having a contact surface 534, where contact surface 534 faces block assembly 510, carrier 512, cases 514 and sample holders 516. Heated cover 530 can also include a platen 536, a heat source 540 to heat platen 536, a sealing element 538, and transparent plates 542 for passage of light from the optical system to the samples in sample holders 516 (refer to FIG. 11 as well). Carrier 512, when positioned on a top surface 511 of block assembly 510, can be configured to receive sample holders 516 and align sample holders 516 with transparent plates 542 to allow the samples on the holders to receive the light from the optical system passing through the plates.

Carrier 512 can also include rims (not pictured) on inner walls 515 of the carrier frame, the rims configured to receive sample holders 516 deposited into carrier 512 such that the holders will sit in place on in the carrier even when the carrier is not in place on block assembly. The rims, for example, allow for transport (manual or automated transport) of carrier 512, with holders 516 in place in carrier 512, from a filling station to system 500 for thermal cycling.

Top surface 511 can also provide a relief or multiple reliefs projecting from top surface 511 and shaped to match the dimensions of the respective sample holders 516, such that when carrier 512 meets block assembly 510, the reliefs will displace sample holders 516 from carrier 512 and maintain holders 516 separate from carrier 512 during cycling. Such separation of carrier from holders during cycling can assist in reducing any thermal non-uniformity caused by carrier 512 contact with holders 516.

Sealing element 538 can be provided on contact surface 534 such that sealing element 538 contacts block assembly 510, or carrier 512, to form an enclosed volume of air between sample holders 516 and platen 536. In certain embodiments, contact surface 534 directly contacts either block assembly 510 or carrier 512.

Figure 10A:
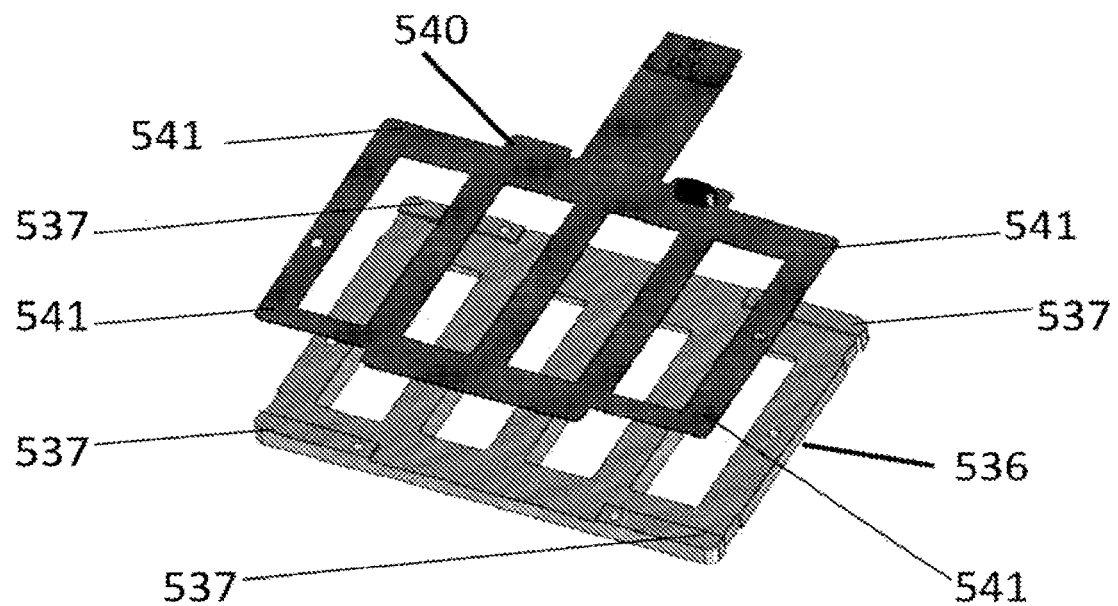
FIG. 10A is an exploded top perspective view of a heat source according to an embodiment of the present invention.
Figure 10B:
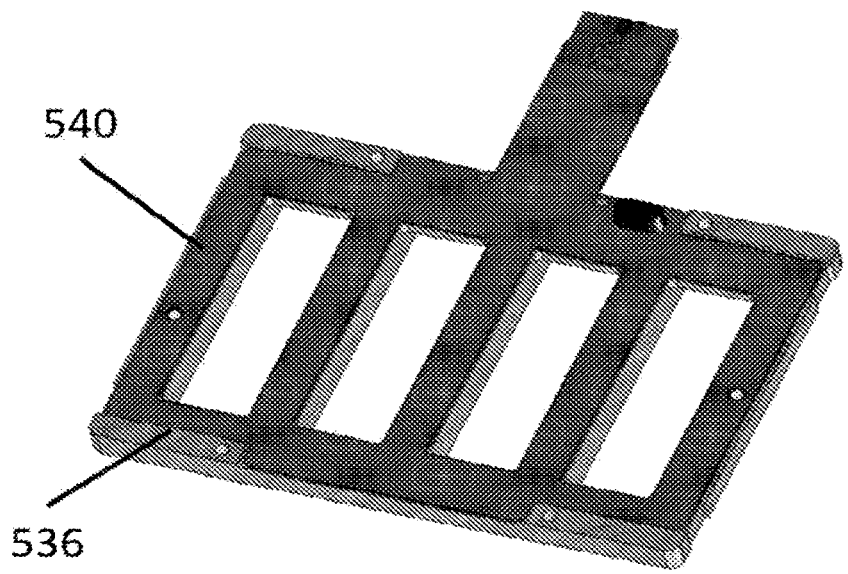
FIG. 10B is a top perspective view of a connected heat source according to an embodiment of the present invention.

Heat source 540 can operate to heat the enclosed volume of air to prevent condensation on the one or more cases 514. The heat from heat source 540 can also prevent thermal non-uniformity of sample holders 516 when the sample holders are cycled through a series of temperatures. Thermal non-uniformity causes samples to vary in cycling temperatures based on their orientation on the sample holders. Prevention of said thermal non-uniformity is a key feature in providing consistent thermal cycling and consistent corresponding test results. An example orientation of platen 536 and heat source 540 is provided in FIGS. 10A and 10B. In particular, FIG. 10A illustrates platen 536 and heat source 540 as unconnected and FIG. 10B illustrates heat source 540 on platen 536 in a final connected orientation for inclusion in the block assembly. Platen 536 can include platen edges 537 and heat source can include heater edges 541.

Heat source 540 can be a single heating element or more than one heating element. Heat source 540 can include one heating zone with one temperature sensor such as, for example, a single thermistor. Heat source can include multiple heating zones having multiple temperature sensors. Each heating zone of the multiple heating zones can have its own associated temperature sensor. Multiple heating zones can be provided in a single heating element or in multiple heating elements. For example, each heating element of the multiple heating elements can serve as one of a plurality of heating zones such that each zone can be controlled independently. By providing a heating element or multiple heating elements that make up the plurality of heating zones, the temperature of each heating zone can be controlled so as to minimize thermal non-uniformity (TNU) in heated cover 530.

In certain embodiments, TNU can be minimized by varying the thicknesses of platen 536, heat source 540, or both platen 536 and heat source 540. For example, platen thickness can be decreased to decrease the mass between heat source 540 and the samples, thus increasing the amount of heat that can transfer between heat source 540 and the samples. TNU can also be minimized by increasing the thickness of heat source 540 to increase the heat being transferred to the samples. In certain embodiments, the thickness of both platen 536 and heat source 540 can be altered to minimize TNU.

In an embodiment, platen thickness can be decreased at platen edges 537 to minimize edge effects (such as lost heat, for example), thus increasing the amount of heat that can transfer between heat source 540 and the samples at edges 537 to better match the heat transfer through the remainder of platen 536. TNU can also be minimized by increasing the thickness of heater edges 541 of heat source 540 to increase the heat being transferred to the samples. By increasing the thickness of heater edges 541, the heat source is strengthened at edges 541 to offset edge effects such as, for example, lost heat due to proximity to ambient conditions. In certain embodiments, the thickness of both platen edges 537 of platen 536 and heater edges 541 of heat source 540 can be altered to minimize TNU.

In another embodiment, and illustrated in FIG. 9A, sealing element 538 can, for example, be a gasket formed to contact surface 534 of frame 532. When gasket 538 contacts block assembly 510, for example, gasket 538 will contact either the block assembly itself or carrier 512. Heated cover 530 can engage block assembly 510 by moving the heated cover to block assembly 510, by moving block assembly 510 to meet heated cover 530, or by moving both the heated cover and the block assembly to meet each other. In this embodiment, gasket does not contact cases 514 or sample holders 516 to form the enclosed volume. Besides a gasket, sealing element 538 can also be any kind of sealing material capable of forming and maintaining a seal with block assembly 510, such as, for example, a spring element or group of spring elements. The spring element can be, for example, a leaf spring or group of leaf springs.

In other embodiments, contact surface 534 and/or sealing element 538 can be located specifically to contact cases 514 or sample holders 516 to seal the sample holders 516 themselves. For example, sample holders can have individual reaction sites sealed by reaction site covers including, but not limited to, caps, film, glass and plastic. The pressure of heated cover 530, facilitated by contacting surface 534 and/or sealing element 538 with cases 514 or sample holders 516, can apply pressure to sample holders 516, and their respective reaction site covers, to assist in maintaining sealed reaction sites.

Figure 9B:
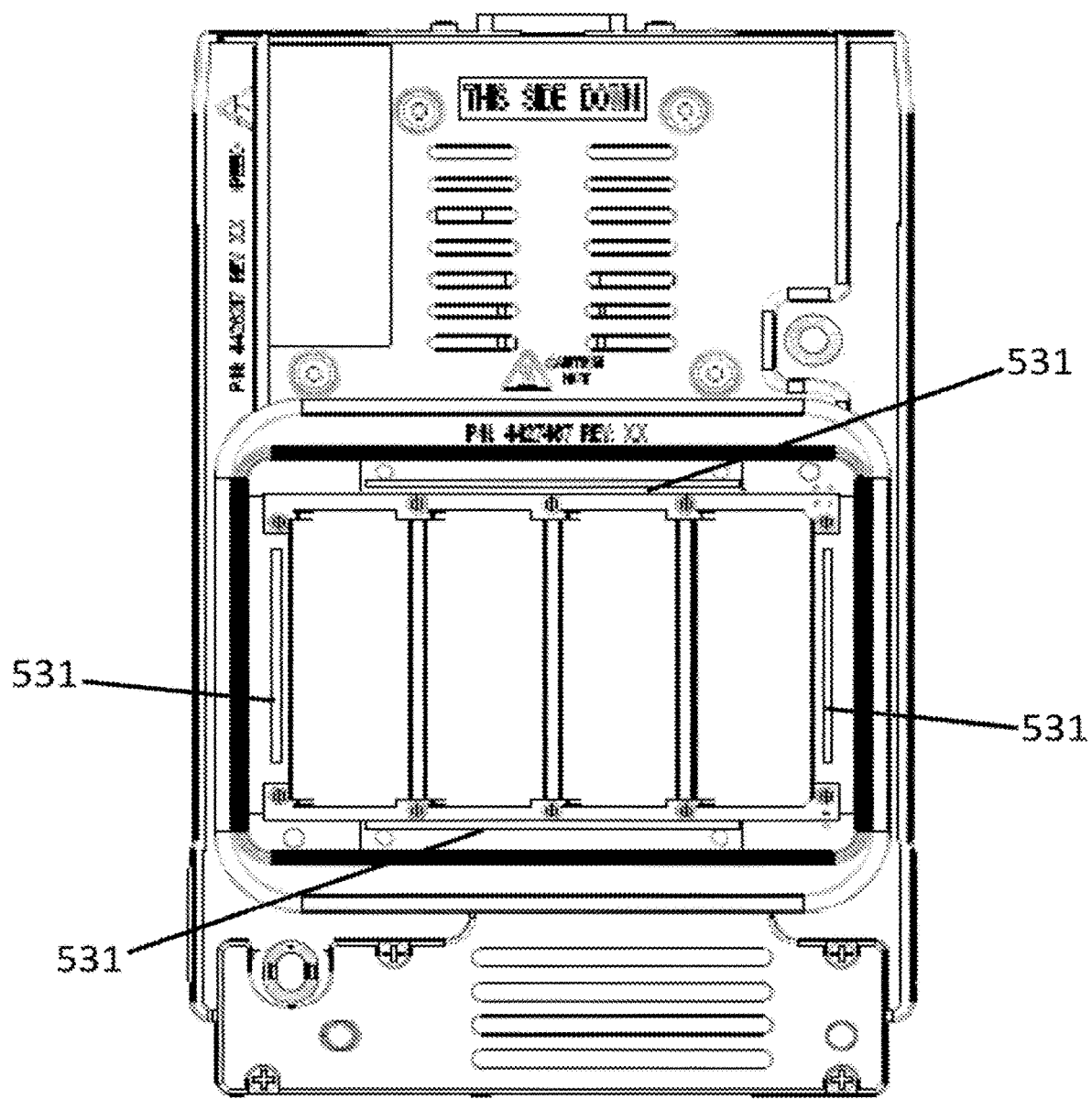
FIG. 9B is a bottom view of a heated cover according to an embodiment of the present invention.

Referring now to FIG. 9B, rather than using a sealing element or contact surface to form the enclosed volume between the heater cover platen and the sample holders, contact projections 531 can contact an edge 513 on carrier 512 (see FIG. 9A) to form the enclosed volume.

Figure 11:
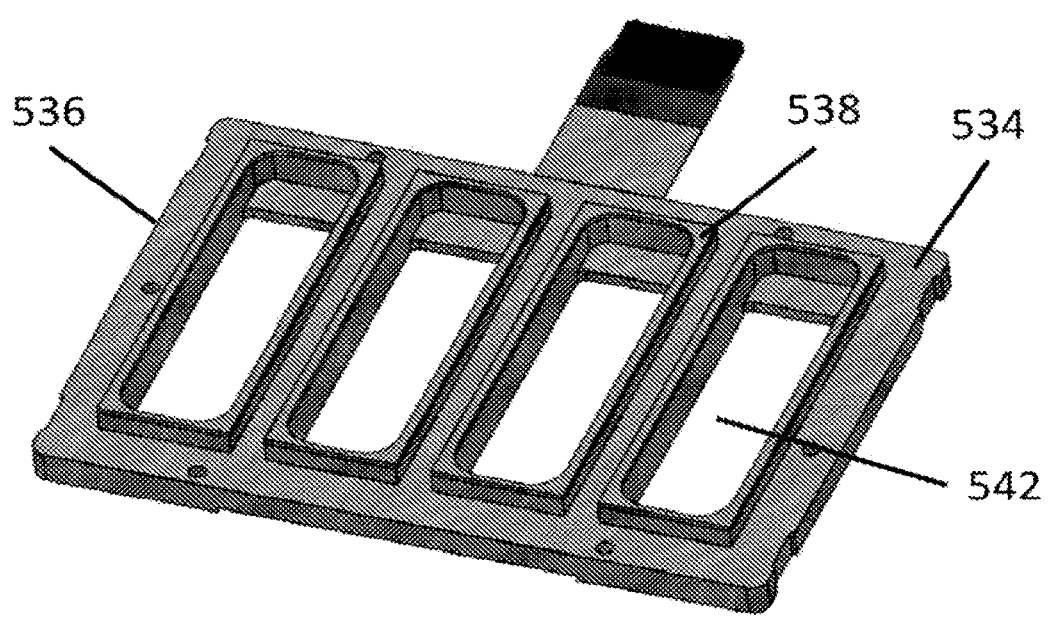
FIG. 11 is a bottom perspective view of a connected heat source according to an embodiment of the present invention.

In another embodiment, illustrated in FIG. 11, sealing material 538 can be a compliant material formed to a contact surface 534 located on the outside of transparent plates 542. Compliant material 538 can be any rubber such as, for example, silicone rubber. Compliant material 538 can be adhered to contact surface 534 using an adhesive such as, for example, cyanoacrylate or any comparable fast-acting adhesive.

In an embodiment, transparent plates 542 can be positioned directly above a corresponding sample holder 516 when cover 530 is in place over block assembly 510. Moreover, at least one of transparent plates 542 can have substantially the same dimensions as corresponding sample holder 516. In another embodiment, each transparent plate 542 can have substantially the same dimensions as corresponding sample holder 516. In yet another embodiment, one or more transparent plates 542 are positioned at an angle relative to its corresponding sample holder 516. The angle of the transparent plate prevents reflection of light passing through the one or more transparent plates from the excitation source of the optical system. For example, the angle can be between three and eight degrees. In a further embodiment, the transparent plates are glass plates High Density Filler In an embodiment, a filling apparatus can be used to load a plurality of samples into wells of a respective sample holder. In the case of a through-hole array, an automatic filling apparatus is advantageous because of the very small size of the array wells and the corresponding difficulty of loading samples, particularly if there are a variety of samples to load into sample holders. Various aspects and advantages of a filling apparatus for loading biological samples onto a sample holder are further disclosed in U.S. Ser. No. 11/393,047, the entire contents of each of which are hereby incorporated by reference in its entirety for all purposes as if fully set forth herein.

Figure 12:
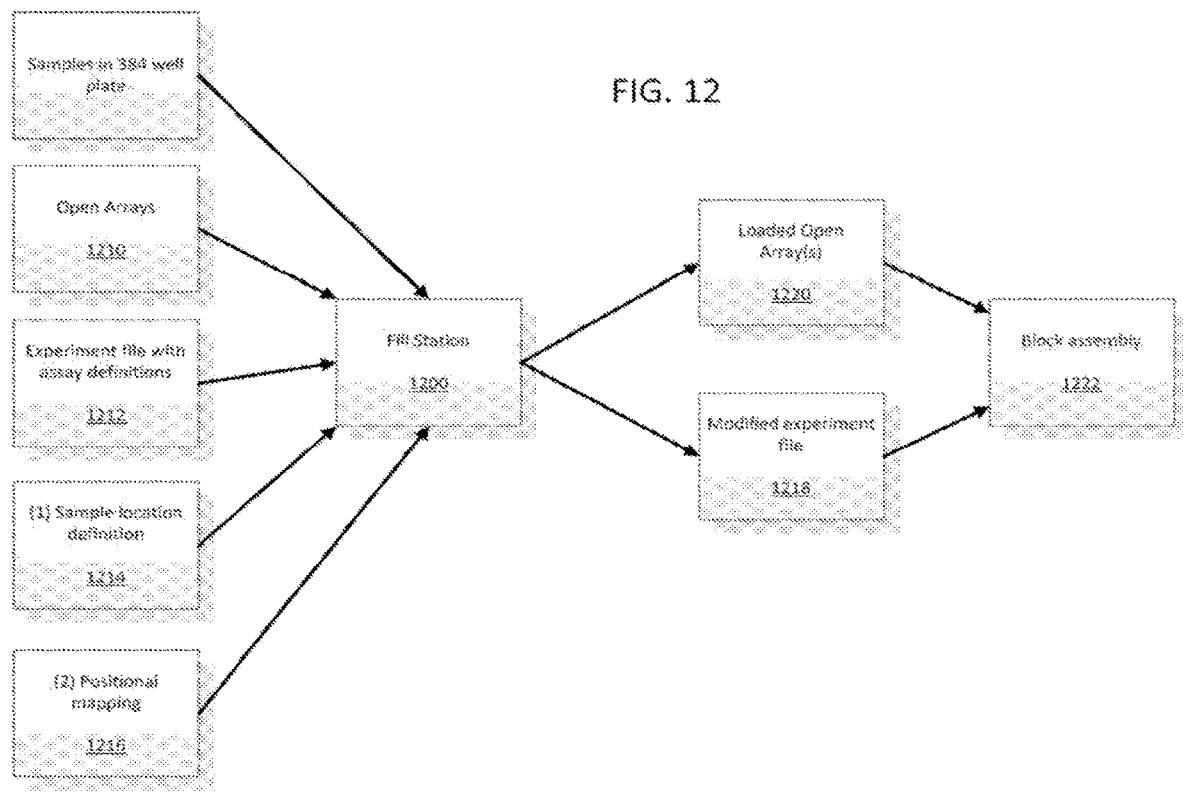
FIG. 12 is a flow diagram illustrating a workflow between a fill station and a block assembly according to an embodiment of the present invention.

In an embodiment, a data file is provided having instructions for arranging the plurality of samples onto a plurality of sample locations, or wells, on the one or more sample holders. The fill station includes a processor configured to execute the instructions, with the fill station thereinafter loading each sample holder with the plurality of samples according to the executed instructions. FIG. 12 provides a flow chart for the workflow of loading samples into through-hole sample holders ("open arrays") at the fill station and transferring loaded sample holders to a block assembly for thermal cycling.

In the flow chart of FIG. 12, a fill station 1200 receives open arrays 1210 for loading. Fill station 1200 also receives the aforementioned data file 1212. Data file 1212 can contain instructions such as, for example, sample loading instructions, assay definitions for each sample, sample location definitions, positional mapping instructions, or combinations thereof. Assay definitions can include the type of assay to be run on each sample. Sample location definitions can include instructions of where on open arrays 1210 to load specific samples. Positional mapping instructions can include instructions for positioning samples onto specific open arrays. Sample location definitions and positional mapping instructions can be provided as parts of data file 1212 or as separate files 1214 and 1216. Based on the instructions provided in combination with the number of open arrays used in fill station 1200, the fill station loads samples into the open arrays to meet the given parameters.

All of the aforementioned instructions can be provided to fill station 1200 from a variety of sources including, for example, an external computer system, a remote monitoring device, a server, a cd-rom, or flash memory. Instructions can also be provided from user direct input into an interface on fill station 1200.

In an embodiment, the cases holding open arrays 1210 can be constructed and arranged to accept a case cover to enclose each of the loaded sample holders and provide a sealed interior within each case and corresponding case cover. The case cover or the case itself can also be configured to receive a liquid that is immiscible with the samples into the sealed interior. The immiscible liquid can be, for example, a perfluorinated hydrocarbon, a hydrocarbon, an oil, or a silicone fluid. The liquid can be introduced into the case interior by providing, for example, a fill port or injection location on the case or case cover. The port or injection location can be sized to receive a syringe for the introduction of the immiscible liquid. The port or injection location can further be configured to be plugged after immiscible liquid introduction to trap the liquid in the sealed case interior.

Data file 1212 can then be modified to include the initially provided assay definitions in combination with updated sample and positional locations after sample loading. This modified data file 1218 can be delivered to a block assembly 1222 of a thermal cycler along with the loaded open arrays 1220. In an embodiment, an automated device can be provided for transferring loaded sample holders from the fill station to the block assembly. Such an automated device can be, for example, a robotic arm.

Thermal Cycler Workflow

Figure 13:
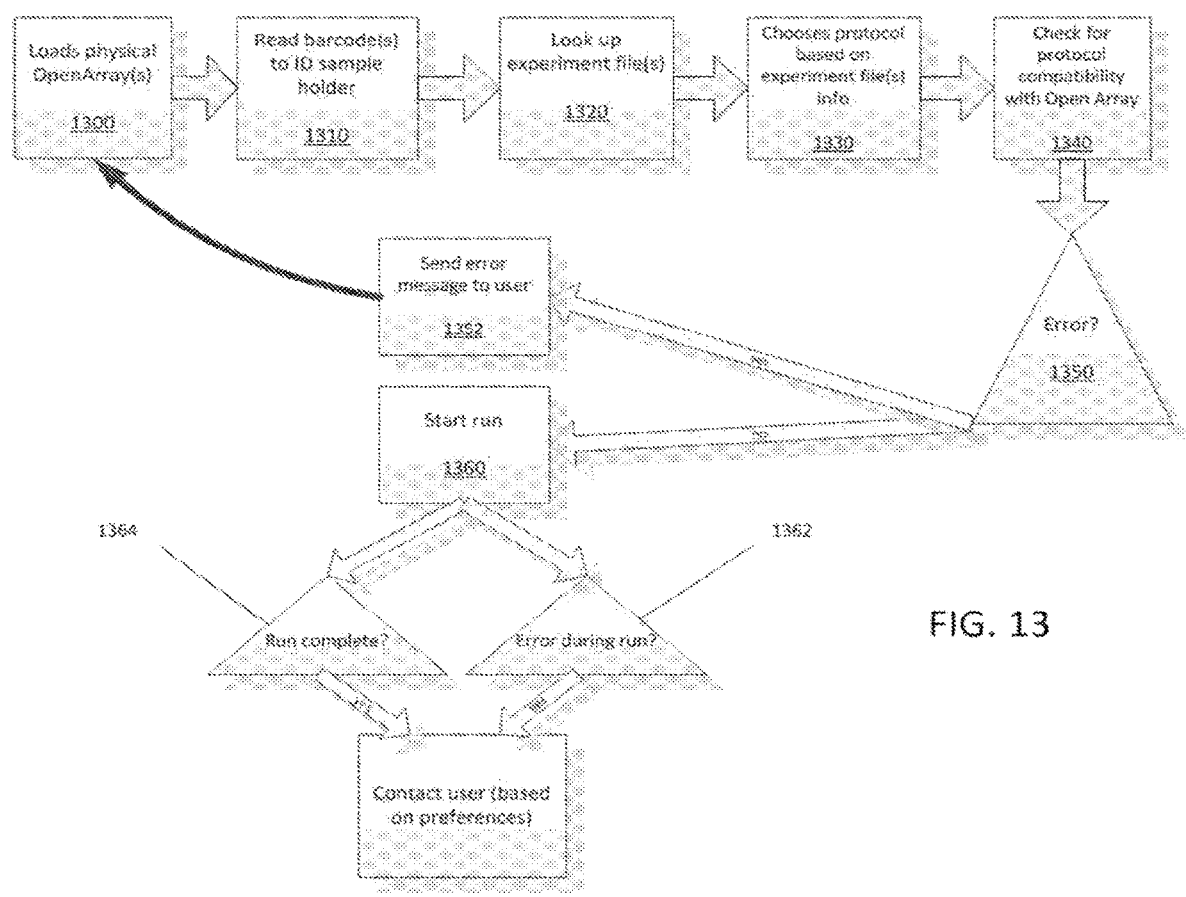
FIG. 13 is a flow diagram illustrating a workflow within a thermal cycler according to an embodiment of the present invention.

Referencing the flow chart of FIG. 13, once the modified data file and loaded open arrays are delivered to the thermal cycler, the thermal cycler is configured to load the open arrays into the block assembly at step 1300. Once loaded, the optical system of the thermal cycler (see FIG. 3) can be configured so that an optical sensor on the optical system (see FIG. 3) may be used to read an identifier on the open array. The identifier can include, for example, characters and/or a barcode on the open array (see FIG. 4). In addition, as discussed previously, the optical system may be configured to provide images that contain either, or both, alphanumeric characters or barcodes for each imaged open array. Such images can be used to confirm, for example, that the one or more open arrays are properly positioned in the block assembly and, as provided at step 1310 of FIG. 13, that the correct open array has been loaded into the block assembly.

At step 1320, a processor/control system on the thermal cycler can look up the delivered modified experimental file for the correct assay definitions in view of the updated sample and positional locations after sample loading. Based on the information and/or instructions provided in the retrieved modified experimental file, the processor/control system on the thermal cycler can choose the appropriate protocol at step 1330 for thermal cycling the loaded samples through a series of temperatures and confirm at step 1340 that the chosen protocol is compatible with the samples loaded in the open arrays.

At step 1350, the processor/control system makes an error determination regarding the compatibility of the chosen protocol with the loaded samples. If there is an error at step 1350, the processor/control system is programmed to deliver an error message to the user as to type of error observed. Error types can include, for example, a missing data or experimental file, an incomplete data or experimental file, or detected difference between assay definition in the data or experimental file and assay definition actually in the through-holes. The error message can be delivered electronically to any location observable by the user. The message can be delivered in any form observable by the user including, for example, text message or email message. Locations, as discussed previously, can include, for example, a user interface integrated on the thermal cycler, an external interface (such as a computer, for example), a remote monitoring device (such as a PDA or laptop, for example) connected directly via an internet connection, or to a web server or distributed network of servers accessible by the user.

At step 1360, if the processor/control system does not observe an error in protocol compatibility, the processor is configured to start the thermal cycling run by cycling the samples through a series of temperatures.

If an error is detected during the thermal cycling run (step 1362), the processor/control system is once again configured to deliver an error message to the user as to type of error observed. Error types can include, for example, a power surge, an instrument failure due to a voltage spike, or an instrument failure due to a thermal inaccuracy.

If the processor/control system detects no error during the run, and the thermal cycler completes the run (step 1364), the processor/control system is programmed to alert the user via message at step 1370. Once again, the message can be delivered in any form observable by the user including, for example, text message or email message, and be delivered electronically to any location observable and accessible by the user.

Figure 14:
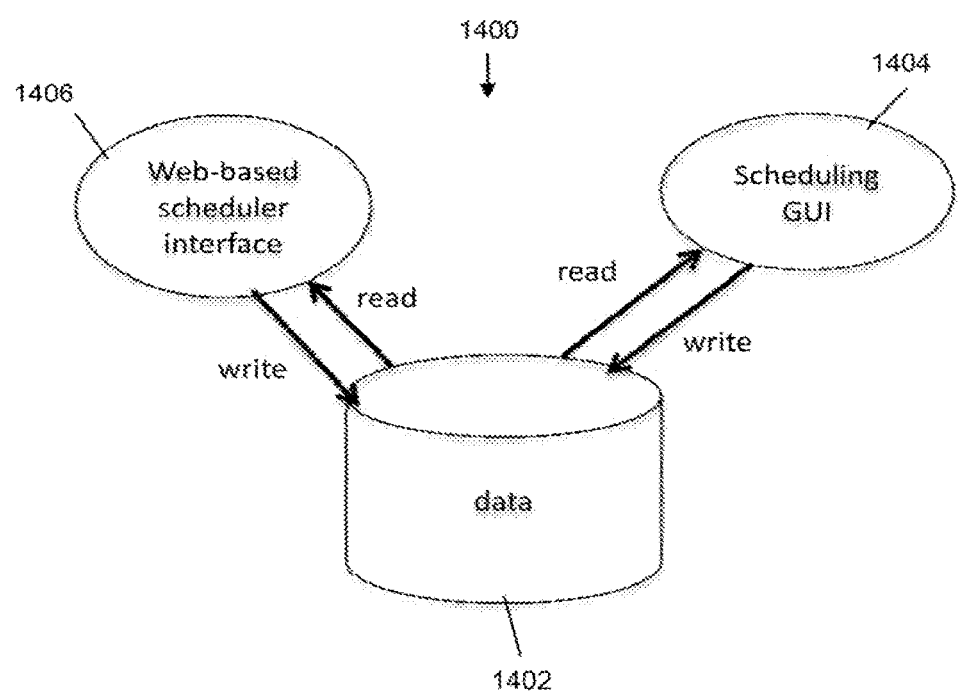
FIG. 14 is a block diagram illustrating a web scheduler system according to various embodiments described herein.

FIG. 14 illustrates a block diagram of a scheduling system 1400 for the instrument according to various embodiments described herein. Scheduling system 1400 may be used by users to reserve time to use an instrument to perform their experiments or testing. According to various embodiments, scheduling system 1400 includes a memory 1402 for storing scheduling data. Memory 1402 may also store instructions executable by a processor for receiving and updating the scheduling data.

Scheduling system 1400 may also include a scheduling graphical user interface (GUI) 1404 for displaying the scheduling data to a user. In some embodiments, the scheduling GUI is included on the instrument. In other embodiments, a scheduling GUI 1404 may be displayed on another computing system connected to, or in communication with, the instrument. Scheduling system 1400 may also include a web-based scheduling interface 1406. The web-based scheduling interface 1406 communicates with a processor of the instrument.

Figure 15A:
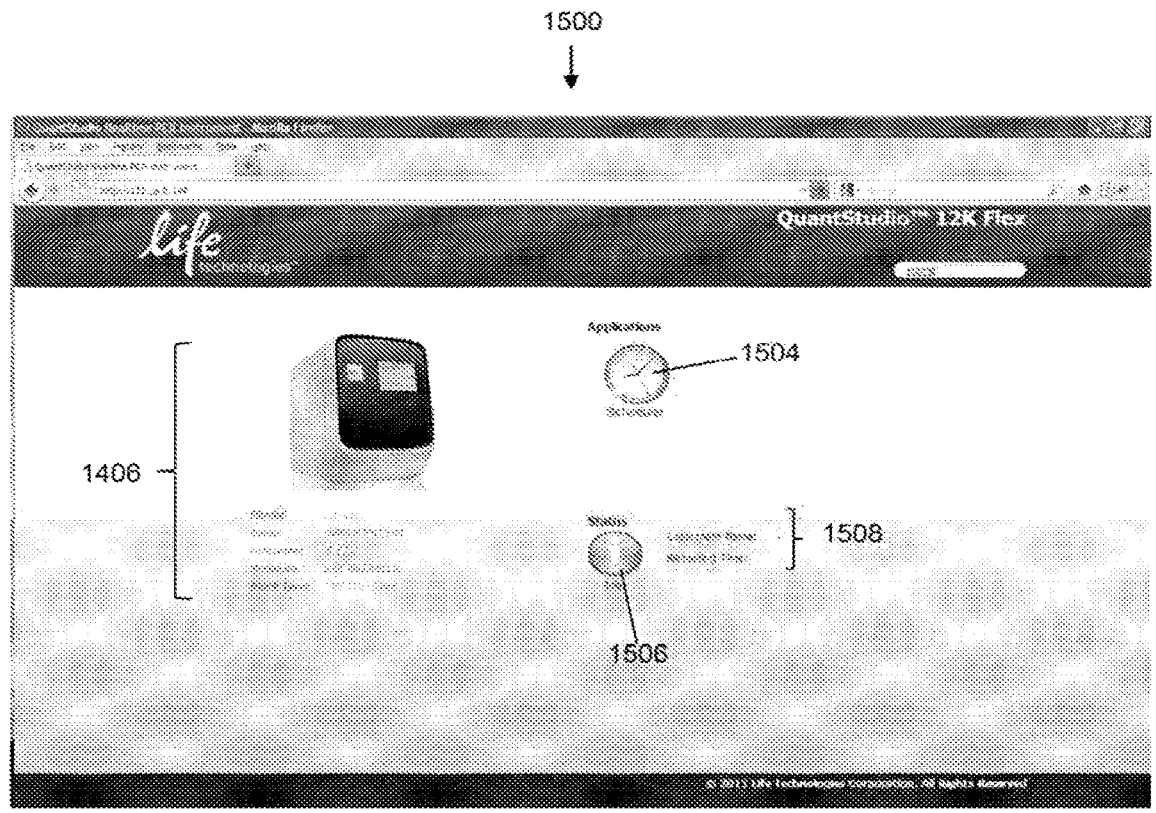
FIG. 15A is an exemplary status graphical user interface (GUI) for a web scheduler system according to various embodiments described herein.

FIG. 15A illustrates an exemplary web-based user interface 1500 to access a scheduling system of an instrument with network capability. The instrument is assigned an IP address according to embodiments described herein. A client browser may access the scheduling system over the Internet, or any client/server system, using the IP address assigned to the biological analysis system. According to the exemplary web-based interface 1500, identifying information 1502 of the instrument may be displayed. According to various embodiments, information may include a model number, a name, operating firmware version, serial number, and block type, for example. The scheduling data may also be accessed by selecting the scheduling application by clicking icon 1504.

Furthermore, as mentioned above, the status of the instrument may be indicated by icon 1504. In the example shown in FIG. 15A, the status icon 1506 shows the instrument is idle. Web-based user interface 1500 may also display experiment information 1508, including the experiment name being run on the instrument and the remaining time left for the instrument to complete its run. In various embodiments, the web-based interface 1500 may allow the user to monitor, in real-time, the progress of the experiment being run on the instrument. For example, the user may be able to access and view amplification data of the samples being thermal cycled in the instrument.

Figure 15B:
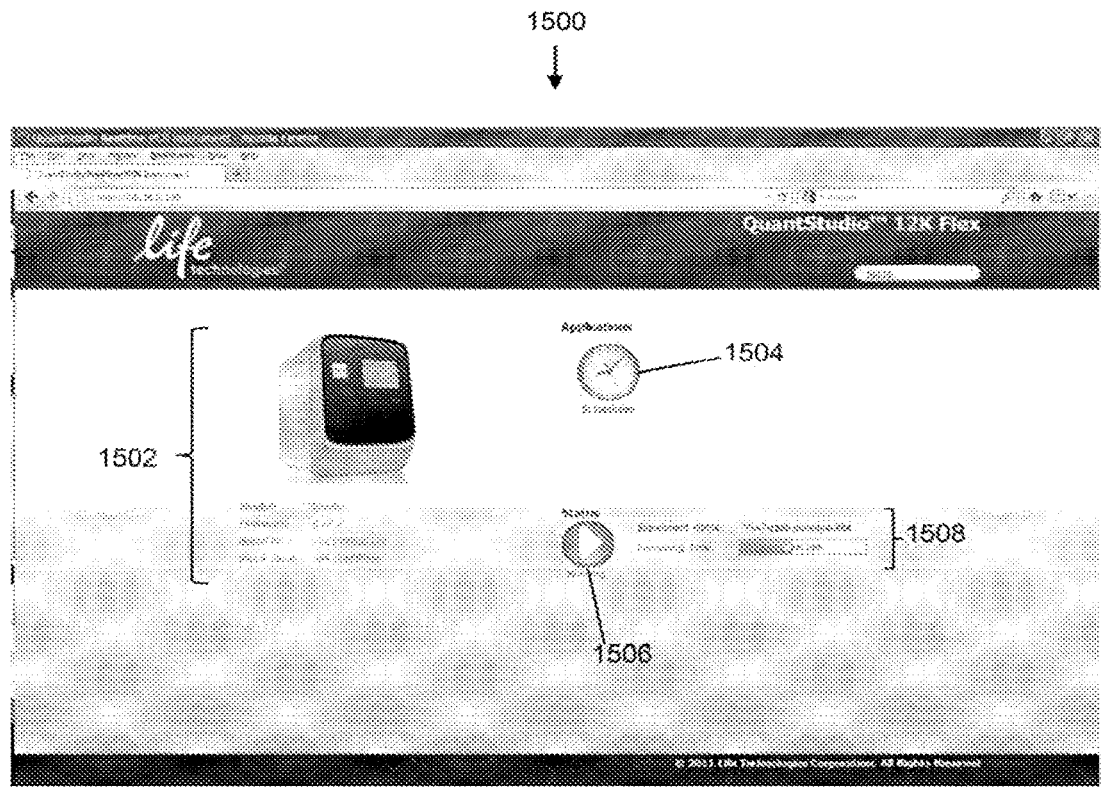
FIG. 15B is another exemplary status GUI for a web scheduler system according to various embodiments described herein.

FIG. 15B shows another example of web-based user interface 1500. Here, status icon 1504 indicates the instrument is currently running. Experiment information 1508 shows the name of the experiment running as wells as the progress, or remaining time left before the experiment is finished.

Figure 16:
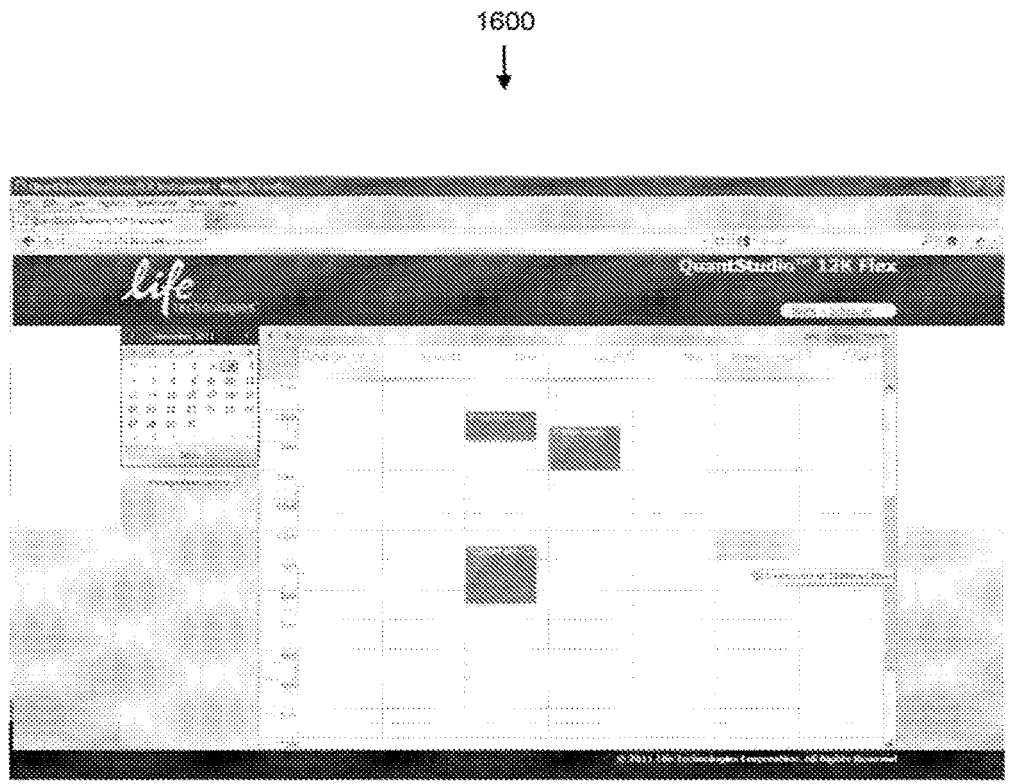
FIG. 16 is an exemplary calendar GUI according to various embodiments described herein.

FIG. 16 shows a web-based scheduling graphical user interface 1600 according to various embodiments described herein. A user may access scheduling data of an instrument over a network, such as the Internet. The scheduling data indicates the time the instrument is reserved by users.

Figure 17:
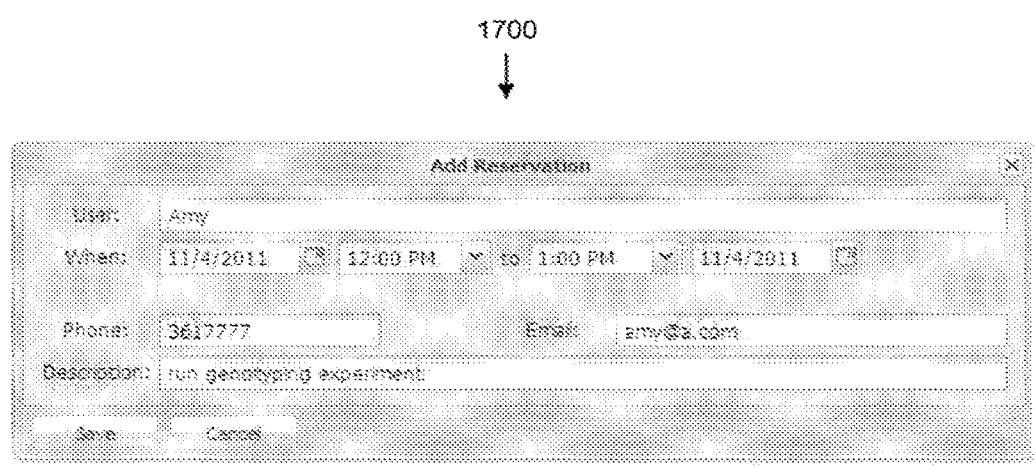
FIG. 17 is an exemplary add reservation GUI according to various embodiments described herein.

FIG. 17 shows an exemplary add reservation GUI 1700. A user may use the add reservation GUI 1700 to enter in the desired time the user would like to reserve the instrument. The user may also input contact information and other notes that may be viewed by other users using the scheduling system.

Further aspects of the present invention can also be described as follows:

In alternative embodiment 1, a biological analysis system is provided, comprising: an interchangeable assembly configured to accommodate any one of a plurality of sample holders, each respective sample holder configured to receive a plurality of samples; a control system configured to cycle the plurality of samples through a series of temperatures; and an optical system configured to detect fluorescent signals emitted from the plurality of samples, wherein the optical system comprises: a single field lens; an excitation source; an optical sensor; and a plurality of filter components.

In alternative embodiment 2, the biological analysis system of embodiment 1 is provided, wherein the plurality of sample holders are selected from the group consisting of a 96-well block, a 384-well block, a low-density array, and a through-hole array.

In alternative embodiment 3, the biological analysis system of any of the preceding embodiments is provided, wherein the optical system is further configured to confirm that the sample holder is properly positioned on the interchangeable assembly.

In alternative embodiment 4, the biological analysis system of any of the preceding embodiments is provided, wherein the sample holder further comprises an identifier that references a data file storing data related to the sample holder, and wherein the optical system is further configured to image the identifier to confirm that the correct sample holder is positioned on the interchangeable assembly.

In alternative embodiment 5, the biological analysis system of any of the preceding embodiments is provided, wherein the excitation source is one or more light emitting diodes.

In alternative embodiment 6, the biological analysis system of any of the preceding embodiments is provided, further comprising a temperature control system configured to maintain the excitation source within a defined temperature range.

In alternative embodiment 7, the biological analysis system of any of the preceding embodiments is provided, further comprising a temperature control system comprising a fan configured to operate intermittently to maintain the excitation source within a defined temperature range.

In alternative embodiment 8, the biological analysis system of any of the preceding embodiments is provided, wherein the field lens is a bi-convex lens.

In alternative embodiment 9, the biological analysis system of any of the preceding embodiments is provided, wherein the sample holder is a through-hole array.

In alternative embodiment 10, the biological analysis system of any of the preceding embodiments is provided, wherein the sample holder is a through-hole array comprising 48 locations, each location including a subarray having dimensions of 8 through holes by 8 through holes.

In alternative embodiment 11, a biological analysis system is provided, comprising: a thermal cycler comprising: a block assembly configured to receive a plurality of samples and cycle the plurality of samples through a series of temperatures; an optical system comprising an optical sensor configured to detect a fluorescence level emitted from each of the plurality of samples; a user interface integrated on an exterior surface thermal cycler device; and a processor programmed to process the detected fluorescence levels and display the fluorescence levels on the integrated user interface in real-time, wherein the parameters for displaying fluorescent levels are changeable based on user preference.

In alternative embodiment 12, the biological analysis system of embodiment 11 is provided, wherein the parameters are selected from the group consisting of a selection of one or more sample holders that receive the plurality of samples, a selection one or more wells within the one or more sample holders, a selection of one or more dyes within the one or more wells, and combinations thereof.

In alternative embodiment 13, the biological analysis system of any of embodiments 11-12 is provided, wherein one or more sample holders are provided and are selected from the group consisting of a 96-well block, a 384-well block, a low-density array, and a through-hole array.

In alternative embodiment 14, the biological analysis system of any of embodiments 11-13 is provided, wherein the processor is programmed to display the fluorescence levels in the form of real-time amplification plots.

In alternative embodiment 15, the biological analysis system of any of embodiments 11-14 is provided, wherein the block assembly is an interchangeable block assembly and is configured to accommodate any one of a plurality of sample holders selected from the group consisting of a 96-well block, a 384-well block, a low-density array, and a through-hole array, and wherein the processor is programmed to display the fluorescence levels in the form of real-time amplification plots for any one of the plurality of sample holders.

In alternative embodiment 16, a biological analysis system is provided, comprising: a block assembly configured to accommodate one or more cases, wherein each case configured accommodate a sample holder that receives a plurality of samples; a cover comprising: a frame having a contact surface; a platen; a sealing material configured to contact the block assembly to form an enclosed volume of air between the sample holders and the platen; and a heat source configured to heat the enclosed volume of air to prevent (a) condensation on the one or more cases and (b) thermal non-uniformity of the sample holders when the sample holders are cycled through a series of temperatures.

In alternative embodiment 17, the biological analysis system of embodiment 16 is provided, wherein the sealing material is a gasket formed to the contact surface of the frame.

In alternative embodiment 18, the biological analysis system of any of embodiments 16-17 is provided, wherein the sealing material is a gasket configured and arranged to contact the block assembly and not contact the sample holders.

In alternative embodiment 19, the biological analysis system of any of embodiments 16-18 is provided, wherein the block assembly further comprises a carrier shaped to accommodate the one or more cases, wherein the sealing material is arranged to form to the carrier.

In alternative embodiment 20, the biological analysis system of any of embodiments 16-19 is provided, wherein the one or more cases include a thermally conductive material.

In alternative embodiment 21, the biological analysis system of any of embodiments 16-20 is provided, wherein the one or more cases include a thermally conductive material selected from the group consisting of aluminum, graphite, zinc, berilium, stainless steel, and combinations thereof.

In alternative embodiment 22, the biological analysis system of any of embodiments 16-21 is provided, wherein the platen comprises one or more transparent plates each positioned directly above a corresponding sample holder.

In alternative embodiment 23, the biological analysis system of any of embodiments 16-22 is provided, wherein the platen comprises one or more transparent plates each having substantially the same dimensions as the corresponding sample holder.

In alternative embodiment 24, the biological analysis system of any of embodiments 16-23 is provided, wherein the platen comprises one or more transparent plates each positioned at an angle relative to the sample holder to prevent reflection of light passing through the one or more transparent plates.

In alternative embodiment 25, the biological analysis system of any of embodiments 16-24 is provided, wherein the platen comprises one or more transparent glass plates.

In alternative embodiment 26, a biological analysis system is provided, comprising: a block assembly configured to accommodate one or more cases, wherein each case is configured to accommodate a sample holder loaded with a plurality of samples; a data file having instructions for arranging the plurality of samples onto a plurality of sample locations on the one or more sample holders; and a fill station having a processor configured to execute the instructions, wherein the fill station is configured to load each sample holder with a plurality of samples according to the executed instructions.

In alternative embodiment 27, the biological analysis system of embodiment 26 is provided, wherein each of the one or more cases are constructed and arranged to accept a case cover to enclose each of the loaded sample holders and provide a sealed interior within each case and corresponding case cover.

In alternative embodiment 28, the biological analysis system of any of embodiments 26-27 is provided, wherein each case or each of a corresponding case cover is configured to receive a liquid that is immiscible with the samples into the sealed interior.

In alternative embodiment 29, the biological analysis system of any of embodiments 26-28 is provided, further comprising an automated device for transferring loaded sample holders from the fill station to the block assembly.

In alternative embodiment 30, the biological analysis system of any of embodiments 26-29 is provided, the instructions selected from the group consisting of sample loading instructions, assay definitions for each sample, sample location definitions, and combinations thereof.

In alternative embodiment 31, the biological analysis system of any of embodiments 26-30 is provided, wherein at least one sample holder comprises an identifier.

In alternative embodiment 32, the biological analysis system of any of embodiments 26-31 is provided, further comprising an identifier comprising a barcode.

In alternative embodiment 33, the biological analysis system of any of embodiments 26-32 is provided, wherein the processor is configured to modify the received data file with information selected from the group consisting of updated sample locations, updated positional locations, and combinations thereof.

In alternative embodiment 34, the biological analysis system of any of embodiments 26-33 is provided, wherein each case or each of a corresponding case cover is configured to receive a liquid that is immiscible with the samples into the sealed interior, wherein the immiscible liquid is a perfluorinated hydrocarbon, a hydrocarbon, an oil, or a silicone fluid.

In alternative embodiment 35, a biological analysis system is provided comprising: a block assembly configured to accommodate one or more sample holders loaded with a plurality of samples, wherein the sample holders includes an identifier; a data file which stores instructions; an optical system configured to (a) detect fluorescent signals emitted from the plurality of samples and (b) image the identifier to identify the data file and identify the sample holder; and a processor that executes instructions of the identified data file to cycle the plurality of samples though a series of temperatures.

In alternative embodiment 36, the biological analysis system of embodiment 35 is provided, wherein the instructions are selected from the group consisting of sample loading instructions, assay definitions for each sample, sample location definitions, and combinations thereof.

In alternative embodiment 37, the biological analysis system of any of embodiments 35-36 is provided, wherein the identifier is a barcode.

The descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

What is claimed is:

1. A biological analysis system comprising:
a thermal cycler device comprising:
a block assembly configured to removably receive one or more sample holders chosen from any of a plurality of different types of sample holders, wherein in a state of the one or more sample holders received by the block assembly, the block assembly is in thermal communication with the one or more sample holders and is configured to cycle the one or more sample holders through a series of temperatures;
an optical system comprising an optical sensor configured to detect fluorescence, the optical sensor arranged to detect fluorescence levels emitted from the one or more sample holders when in the received state by the block assembly;
a user interface comprising a display screen coupled to an exterior of the thermal cycler device, the user interface receptive to an input of a selection of a type of sample holder from a plurality of different types of sample holders, the plurality of different types of sample holders comprising two or more of a well plate, a low-density microcard array, and a through-hole high-density array; and
a processor operably coupled to the optical system and the user interface, the processor programmed to:
receive the selection of the type of sample holder,
process the detected fluorescence levels, and
cause display of data corresponding to the fluorescence levels on the display screen of the user interface in real-time based on the input of the selection of the sample holder type.

2. The biological analysis system of claim 1, wherein the optical system comprises:
an excitation source; and
a plurality of filter components.

3. The biological analysis system of claim 2, wherein the excitation source comprises one or more light emitting diodes.

4. The biological analysis system of claim 2, wherein the optical system further comprises single bi-convex field lens positioned to intercept and pass excitation energy from the excitation source and emission energy from the one or more sample holders.

5. The biological analysis system of claim 1, wherein the plurality of different types of sample holders comprise a 96-well plate, a 384-well plate, the low-density microcard array, and the through-hole high-density array.

6. The biological analysis system of claim 1, wherein the processor is programmed to cause the display of the data corresponding to the fluorescence levels on the display screen in the form of real-time amplification plots.

7. The biological analysis system of claim 1,
wherein the optical system is positioned to image an identifier on the one or more sample holders when in the received state by the block assembly.

8. The biological analysis system of claim 7, wherein the processor is further programmed to confirm that the one or more sample holders in a received state by the block assembly are properly positioned on the block assembly based on the identifier.

9. The biological analysis system of claim 7,
wherein the processor is programmed to confirm the input of the selection of the type of sample holder at the user interface is compatible with the imaged identifier.

10. The biological analysis system of claim 1, wherein the processor is further programmed to modify a data file based on the input of the selection of the type of sample holder.

11. The biological analysis system of claim 10, wherein the data file comprises locations of a plurality of reaction sites associated with the type of sample holder corresponding to the selection at the user interface.

12. The biological analysis system of claim 1,
wherein the processor is programmed to cause the display of the data corresponding to the fluorescent levels on the display screen in the form of a plurality of amplification curves.

13. The biological analysis system of claim 12,
wherein the user interface is further receptive to receive a second input of a selection of an amplification curve of the plurality of amplification curves, and
wherein the processor is further programmed to cause an update to the display of the data on the display screen based on the second input.

14. The biological analysis system of claim 1, wherein the display screen comprises a touchscreen receptive to the input via touch of the touchscreen.

\* \* \* \* \*

UNITED STATES PATENT AND TRADEMARK OFFICE
CERTIFICATE OF CORRECTION

PATENT NO. : 11,339,425 B2
APPLICATION NO. : 16/382294
DATED : May 24, 2022
INVENTOR(S) : Jacob K. Freudenthal et al.

It is certified that error appears in the above-identified patent and that said Letters Patent is hereby corrected as shown below:

On the Title Page

In Column 1, item (72), in second inventor's residence, Line 2, delete "Menlo parl" and insert --Menlo Park--.

In item (57), at page 2, in the last Line of the Abstract, delete "lends" and insert --lens--.

In the Claims

In Claim 4, at Column 22, Line 43, delete "single" and insert --a single--.

In Claim 13, at Column 23, Line 14, delete "receive".

Signed and Sealed this
Second Day of August, 2022

Katherine Kelly Vidal
*Director of the United States Patent and Trademark Office*